US011113990B2

(12) United States Patent
Fujiki

(10) Patent No.: US 11,113,990 B2
(45) Date of Patent: Sep. 7, 2021

(54) AUSCULTATORY SOUND IDENTIFICATION TRAINING DEVICE AND AUSCULTATORY SOUND IDENTIFICATION TRAINING SYSTEM

(71) Applicant: TELEMEDICA INC., Yokohama (JP)

(72) Inventor: Kiyoshi Fujiki, Yokohama (JP)

(73) Assignee: TELEMEDICA INC.

( * ) Notice: Subject to any disclaimer, the term of this patent is extended or adjusted under 35 U.S.C. 154(b) by 462 days.

(21) Appl. No.: 16/276,625

(22) Filed: Feb. 15, 2019

(65) Prior Publication Data

US 2019/0180647 A1 Jun. 13, 2019

Related U.S. Application Data

(63) Continuation of application No. PCT/JP2017/029481, filed on Aug. 16, 2017.

(30) Foreign Application Priority Data

Aug. 17, 2016 (JP) .............................. JP2016-160259
Dec. 30, 2016 (JP) .............................. JP2016-257489

(51) Int. Cl.
*G09B 23/28* (2006.01)
*G09B 19/00* (2006.01)
(Continued)

(52) U.S. Cl.
CPC .............. *G09B 23/28* (2013.01); *A61B 7/003* (2013.01); *A61B 7/02* (2013.01); *A61B 7/04* (2013.01);
(Continued)

(58) Field of Classification Search
CPC .......... G09B 23/28; G09B 23/30; G09B 9/00; G09B 19/00; H04R 1/02
See application file for complete search history.

(56) References Cited

U.S. PATENT DOCUMENTS 5,397,237 A 3/1995 Dhont et al.
2002/0051959 A1 5/2002 Yoshii et al.
(Continued)

FOREIGN PATENT DOCUMENTS

JP H05-027113 B2 8/1989
JP 2990602 B1 12/1999
(Continued)

OTHER PUBLICATIONS

International Search Report for corresponding International Application No. PCT/JP2017/029481, dated Oct. 3, 2017.
(Continued)

*Primary Examiner* — Timothy A Musselman
(74) *Attorney, Agent, or Firm* — Mori & Ward, LLP

(57) ABSTRACT

An auscultatory sound identification training device includes a sounding body to convert an electric signal related to auscultatory sound information into an auscultatory sound; a vibration member provided to contact the sounding body so that the auscultatory sound generated by the sounding body is transmitted to the vibration member; a cover member made of a resin provided to contact the vibration member so that the auscultatory sound is transmitted to the cover member to output the auscultatory sound; and a case which has a bottom portion and in which the sounding body, the vibration member and the cover member are provided not to contact the bottom portion.

8 Claims, 20 Drawing Sheets

(51) Int. Cl.
*A61B 7/04* (2006.01)
*A61B 7/00* (2006.01)
*A61B 7/02* (2006.01)
*G09B 9/00* (2006.01)
*H04R 1/02* (2006.01)

(52) U.S. Cl.
CPC .............. *G09B 9/00* (2013.01); *G09B 19/00* (2013.01); *H04R 1/02* (2013.01)

(56) References Cited

U.S. PATENT DOCUMENTS

| | | | |
|---|---|---|---|
| 2010/0279262 A1* | 11/2010 | Lecat | A61B 7/00 434/266 |
| 2015/0056592 A1* | 2/2015 | Cowperthwait | G09B 23/288 434/265 |
| 2016/0019818 A1 | 1/2016 | Tobin | |
| 2017/0372639 A1* | 12/2017 | Cowperthwait | G16H 20/40 |

FOREIGN PATENT DOCUMENTS

| | | |
|---|---|---|
| JP | 2000-19952 | 1/2000 |
| JP | 2002-139991 | 5/2002 |
| JP | 3626087 B2 | 5/2002 |
| JP | 3729829 B2 | 8/2005 |
| JP | 4338102 B1 | 10/2009 |
| JP | 3197436 U | 5/2015 |

OTHER PUBLICATIONS

Written Opinion for corresponding International Application No. PCT/JP2017/029481, dated Oct. 3, 2017.
Japanese Office Action for corresponding JP Application No. 2016-257489, dated Dec. 25, 2018 (w/ English machine translation).
Extended European Search Report for corresponding EP Application No. 17841535.2-1122, dated Apr. 7, 2020.
European Patent Office Communication for corresponding EP Application No. 17841535.2-1122, dated Apr. 24, 2020.

* cited by examiner

AUSCULTATORY SOUND IDENTIFICATION TRAINING DEVICE AND AUSCULTATORY SOUND IDENTIFICATION TRAINING SYSTEM

CROSS-REFERENCE TO RELATED APPLICATIONS

The present application is a continuation application of International Application No. PCT/JP2017/029481, filed Aug. 16, 2017, which claims priority to Japanese Patent Application No. 2016-160259 filed Aug. 17, 2016 and Japanese Patent Application No. 2016-257489 filed Dec. 30, 2016. The contents of these applications are incorporated herein by reference in their entirety.

BACKGROUND OF THE INVENTION

Field of the Invention

The present invention relates to an auscultatory sound identification training device and an auscultatory sound identification training system.

Discussion of the Background

Conventionally, in clinical practice, importance of a physical assessment (physical examination technique) for evaluating a health condition of a body of a patient such as detection of a symptom or early detection of abnormality by actually touching the body through interview, inquiry, auscultation, inspection, palpation, etc. has been advocated. Evaluation by physical assessment requires reliable acquisition of base knowledge and technology. To acquire the knowledge and the technology, for example, it is ideal to acquire the knowledge and the technology by actually touching a lot of patients under a leader.

Considering the actual fact that it is difficult to master the knowledge and the technology by actually touching a lot of patients, in general, a doctor, a pharmacist, a nurse, a medical student, a medicine student, or a nursing student learns skills by knowledge acquisition through books or lectures and in exercise form using a simulator simulating the human body under the leader.

In particular, auscultation which is an important element in examination items needs to be absorbed by listening and reliably learning various auscultatory sounds actually using a stethoscope.

JP H05-27113 describes a patient mannequin device used for training of a diagnostic technique by auscultation of a cardiac disease in a medical education course, etc. In this device, in a mannequin doll having only a top body formed of a layer of urethane foam having a thickness of about 20 mm, a speaker is disposed on a back side of the layer of the urethane foam and beating sound of a heart is reproduced from the speaker by an electric signal sent out from the outside of the mannequin doll.

JP 3626087 B2 describes a human body model for auscultatory practice which is used in a case of training diagnosis of auscultation in a medical education process, etc. and in which an outer cover is attached to an outside of a core body made of resin foam to which a speaker connected to a body sound reproduction device is attached. In this human body model for auscultatory practice in which the outer cover is attached to the outside of the core body made of resin foam to which the speaker connected to the body sound reproduction device is attached, a concave portion is formed at an auscultatory site of the core body corresponding to the auscultatory sound, and the speaker having a concave sound reflecting plate attached to the outside is fit into each concave portion so as to be supported by the core body independently of each other. Further, one or two or more sounds selected from pulmonary alveolus sound, heartbeat sound, bronchial sound, and pulsation sound can be reproduced.

JP 3729829 B2 describes a human body mounting fixture for physical examination training aimed at acquiring and improving various medical techniques related to auscultation, palpation, acupressure, and nursing care. This human body mounting fixture includes a mounting fixture body having elasticity formed to be wearable on a human body or a human body model, position identification means attached by being buried or covered over the entire surface of this accessory body to identify a finger of a trainee touching the mounting fixture body or a contact position of a medical instrument operated by the trainee at the time of physical examination simulatively performed by the trainee on the human body or the human body model to which the mounting fixture body is attached, pressure detection means which is attached by being buried or covered over the entire surface of the accessory body and capable of detecting a contact pressure of the contact position identified by the position identification means as a pressure distribution, and analysis means for analyzing medical techniques of the physical examination by the trainee based on the identified contact position and the detected contact pressure, and is provided with a simulated stethoscope connected to the analysis means. Further, a contact position to which an auscultation portion of the simulated stethoscope is applied is identified by the position identification means, and biological sound of a place corresponding to the contact position (for example, heart sound in the case of the heart, etc.) is extracted from biological sound data stored in biological sound storage means in advance and reproduced through a reproduction unit of the simulated stethoscope. In this way, the trainee can detect an exact part of the human body in which the biological sound is heard. In this instance, when the auscultation portion is applied to a place other than the exact part, the biological sound may not be satisfactorily heard, and ambiguous biological sound containing a lot of noise is reproduced.

JP 4338102 B2 describes a speaker system including a plurality of speaker units sharing an internal space as a common back cavity on a surface of one sphere. This speaker system is aimed at improving sound quality over the entire frequency band by a compact, rational, and simple configuration.

JP 3197436 U describes an acoustic equipment teaching material provided with speakers on two sides of a cubic casing. In this teaching material, positions of the attached speakers are selected to allow assembly and processing.

Recently, the importance of physical assessment and implementation thereof have been drawing more attention. However, it is true that the training may not be easily carried out regardless of location or time.

SUMMARY OF THE INVENTION

According to one aspect to the present embodiment, an auscultatory sound identification training device includes a sounding body to convert an electric signal related to auscultatory sound information into an auscultatory sound; a vibration member provided to contact the sounding body so that the auscultatory sound generated by the sounding body is transmitted to the vibration member; a cover member made of a resin provided to contact the vibration member so that the auscultatory sound is transmitted to the cover member to output the auscultatory sound; and a case which has a bottom portion and in which the sounding body, the vibration member and the cover member are provided not to contact the bottom portion.

DESCRIPTION OF THE DRAWINGS

FIGS. 4A and 4B are diagrams schematically illustrating the auscultation speaker, a mounting plate, and a cover member of the auscultatory sound identification training device according to the same embodiment, in which FIG. 4A is a front view and FIG. 4B is a longitudinal sectional view.

FIGS. 15A, 15B and 15C schematically illustrate appearance of the auscultatory sound identification training device according to the same embodiment, in which FIG. 15A is a diagram viewed from a front side, FIG. 15B is a diagram viewed from a rear side, and FIG. 15C is a diagram viewed from a top side.

DESCRIPTION OF THE EMBODIMENTS

Figure 1:
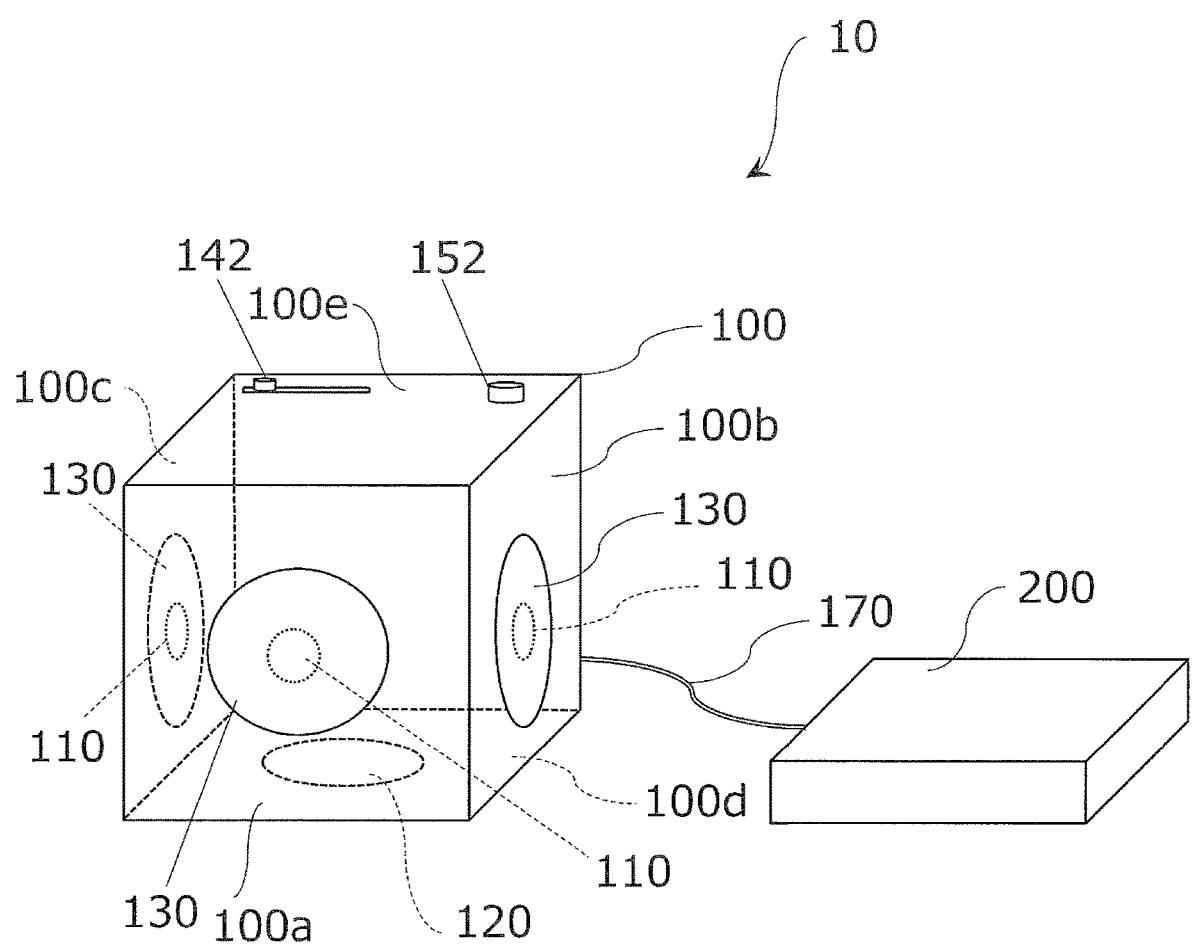
FIG. 1 is a diagram conceptually illustrating an overall configuration of an auscultatory sound identification training system according to a first embodiment of the invention.
Figure 2:
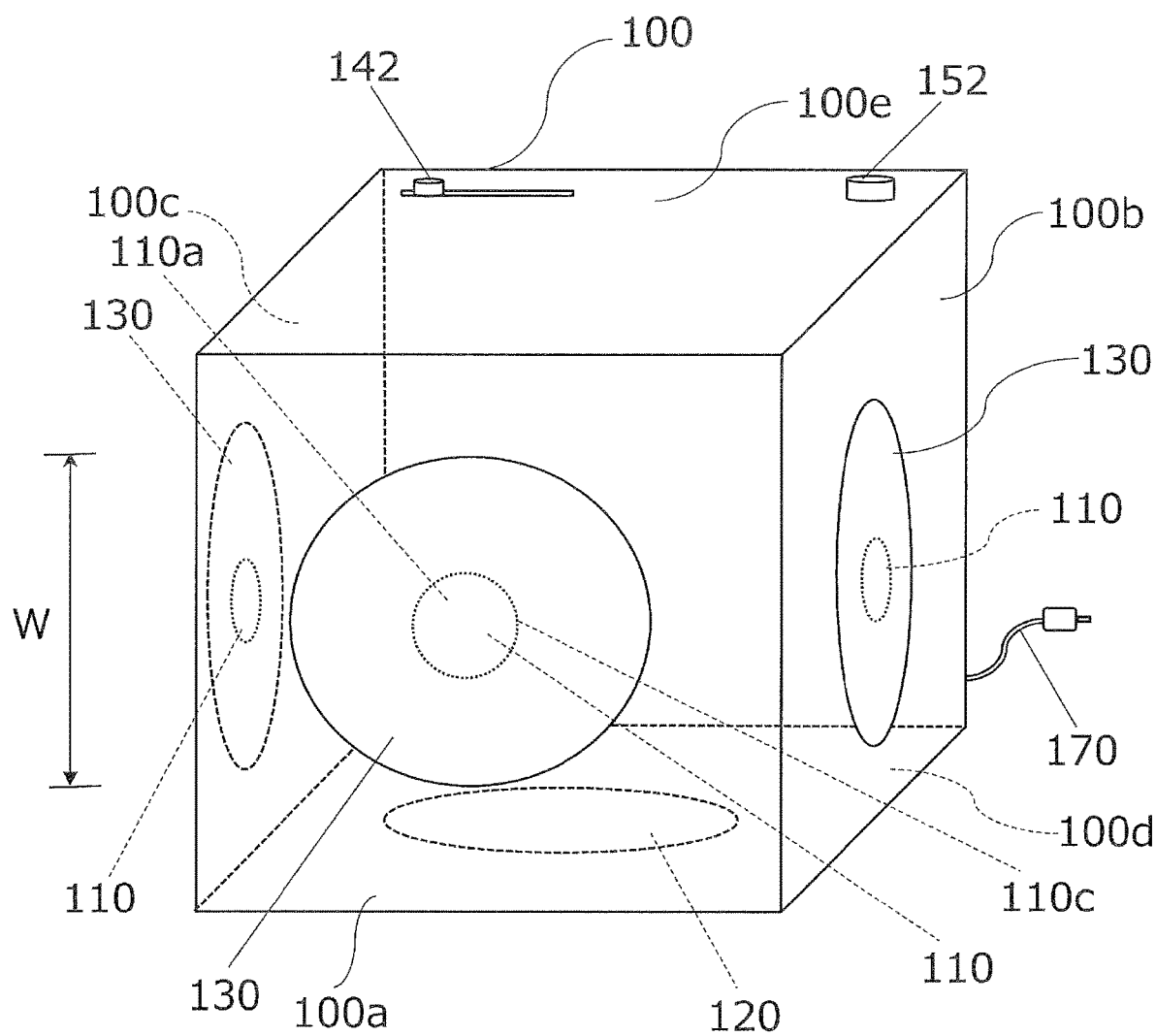
FIG. 2 is a diagram schematically illustrating an auscultatory sound identification training device focusing on an auscultation speaker according to the same embodiment.

Hereinafter, embodiments of the invention will be described with reference to drawings.

First Embodiment

An auscultatory sound identification training system 10 according to the present embodiment is useful for training for indirect auscultation by a stethoscope, and includes an auscultatory sound identification training device 100 and an auscultatory sound generation/management device 200.

The auscultatory sound identification training device 100 has a cubic closed type shape with six square acrylic resin plates each having a thickness of 5 mm and a side of, for example, 100 mm. One auscultation speaker 110 is provided on each of a front portion 100a and side portions 100b and 100c, and a speaker 120 is provided on a bottom portion 100d. Here, a circular auscultation speaker mounting port to which the auscultation speaker 110 is fit and fixed is provided in a center part of each of the front portion 100a and the side portions 100b and 100c. In addition, a circular speaker mounting port to which the speaker 120 is fit and fixed is provided in a center part of the bottom portion 100d.

Further, a volume adjustment slide volume 142 and a changeover button 152 for switching a sound output of auscultatory sound separately for each of the auscultation speaker 110/speaker 120 are provided on an upper portion 100e of the auscultatory sound identification training device 100.

Figure 3:
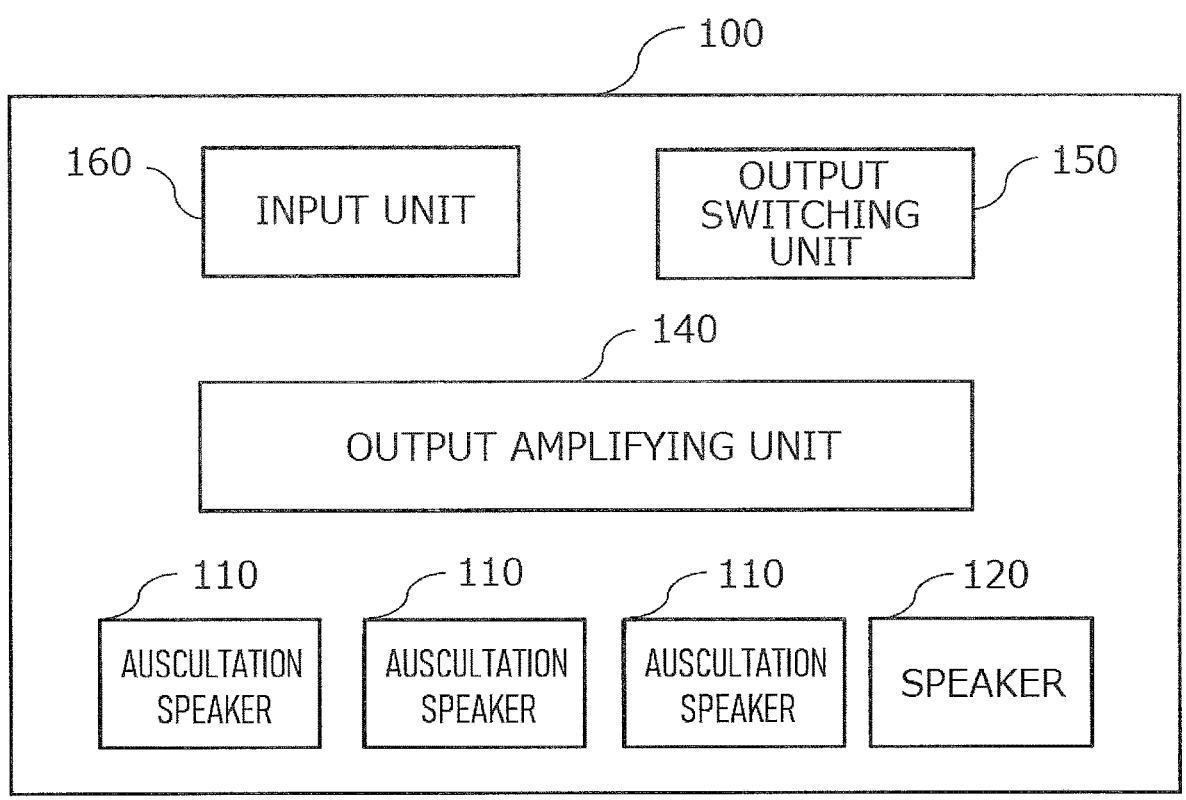
FIG. 3 is a diagram schematically illustrating a functional configuration of the auscultatory sound identification training device according to the same embodiment.

In addition, as illustrated in FIG. 3, an output amplifying unit 140 having the slide volume 142, an output switching unit 150 having the changeover button 152, an input unit 160, and a driving battery unit (not illustrated) for supplying power to the output amplifying unit 140 are disposed in the auscultatory sound identification training device 100.

The auscultation speaker 110 is a small sounding body having a circular shape on the front portion 110a side, a diameter of 22 mm, and a rated input of 0.5 watts. The auscultation speaker 110 includes a magnet and a coil located in a center part 110b and a vibrating plate (vibration member) so-called cone 110c directed outward from the center part 110b as a basic configuration, and converts a sent electric signal related to auscultatory sound information into an acoustic signal to output a sound. In addition, each auscultation speaker 110 is attached by being fit into the auscultation speaker mounting port of each of the front portion 100a and the side portions 100b and 100c as mounting plates such that an outer peripheral portion 110d on the front portion 110a side, that is, an outermost peripheral edge portion of the cone 110c is surrounded.

Further, a cover member 130 made of resin is provided on a surface portion side of the mounting plate, that is, on a surface portion side of each of the front portion 100a and the side portions 100b and 100c to cover the front portion 110a side of the auscultation speaker 110. The cover member 130 has a circular shape having at least a diameter W of 45 mm and is made of a silicone resin having hardness equivalent to that of a human skin. For example, a silicone resin having hardness of 5 to 10 degrees is used. Here, hardness is based on JIS type A in a hardness gauge (hardness tester). In addition, considering prevention of adsorption of dust, etc. due to static electricity, a silicone resin having hardness of about 40 degrees or about 25 degrees may be used. Even though a silicone resin having a thickness of 4 mm is used, the thickness can be appropriately changed. Further, it is considered that hardness of human skin is about 5 to 10 degrees and hardness of the silicone resin is about 5 to 40 degrees as low hardness.

A diameter W of the cover member 130 is set to at least 45 mm since a width of a chest piece (a sound collection surface of the stethoscope) of a general stethoscope is 45 mm. In addition, the cover member 130 is not limited to a circular shape and may have another shape such as an elliptical shape or a quadrangular shape. However, it is necessary to configure the cover member 130 so that a shortest width (short width) of at least the cover member is 45 mm.

The speaker 120 is a sounding body having a circular shape on the front portion side, a diameter of 57 mm, and a rated input of 2 watts, includes a magnet, a coil, and a vibrating plate (vibration member) as a basic configuration, and converts a sent electric signal related to auscultatory sound information into an acoustic signal to output a sound as an auscultatory sound. In addition, the speaker 120 is attached by being fit into the speaker mounting port of the bottom portion 100*d* such that an outer peripheral portion on the front portion side is surrounded.

The output amplifying unit 140 is driven by supply of power from the battery unit and has a function of amplifying the sent electric signal related to the auscultatory sound information and outputting the amplified signal to the auscultation speaker 110 or the speaker 120. The output amplifying unit 140 has the volume adjustment slide volume 142 as described above and may adjust a size of a sound output by the slide volume 142.

The output switching unit 150 has a function of enabling switching of an output destination by an operation of pressing the changeover button 152 as to whether to set a sending destination of the electric signal related to the auscultatory sound information sent from the output amplifying unit 140 to the auscultation speaker 110 or the auscultation speaker 120. For example, the output destination is switched each time the changeover button 152 is pressed such that the output destination is switched from the auscultation speaker 110 when the changeover button 152 is pressed once, from the speaker 120 when the changeover button 152 is pressed once more, and from the auscultation speaker 110 when the changeover button 152 is pressed once more.

It is possible to adopt a configuration in which a control operation is performed such that a different auscultatory sound is output for each of the auscultation speakers 110 and the speaker 120, for example, an auscultatory sound of a right lung is output from a certain auscultation speaker 110/speaker 120, and an auscultatory sound of a left lung is output from another one.

The input unit 160 has a function of receiving an electric signal related to the auscultatory sound information sent via a connection cable 170 and sending the received electric signal to the output amplifying unit 140. In the present embodiment, inputting is performed via the connection cable 170. However, for example, wireless connection may be enabled by infrared communication or wireless communication function by Bluetooth (registered trademark).

A connecting connector is provided at one end of the connection cable 170, and the connection cable 170 is used for connection to the auscultatory sound generation/management device 200 via this connector. Further, the electric signal related to the auscultatory sound information from the auscultatory sound generation/management device 200 is sent to the input unit 160.

The auscultatory sound generation/management device 200 includes a controller 220, an input unit 240, an output unit 260, and a memory 280 disposed therein and is configured to send the electric signal related to the auscultatory sound information to the auscultatory sound identification training device 100 as described above by being connected to the auscultatory sound identification training device 100 via the connection cable 170.

The controller 220 has a function of performing a process of managing/controlling the auscultatory sound information with reference to predetermined program information stored in the memory 280. In addition, the controller 220 has a function of outputting selected auscultatory sound information via the output unit 260 based on input information of an auscultatory sound selection instruction from the input unit 240.

The input unit 240 has a function of storing input information such as an auscultatory sound or an auscultatory sound selection instruction in the memory 280 under management of the controller 220.

The output unit 260 has a function of sending the auscultatory sound information stored in the memory 280 to the outside as an electric signal under management of the controller 220.

The memory 280 is a readable/writable storage device, which stores program information to be referred to by the controller 220 and stores various types of auscultatory sound information. The auscultatory sound information is stored, for example, for each age, gender, body part, degree of obesity, normal sound, and abnormal sound.

With regard to the above configuration, an operation will be described below.

In a case of performing auscultatory sound identification training using the auscultation speaker 110, the changeover button 152 of the auscultatory sound identification training device 100 is pressed to allow sound output from the auscultation speaker 110. Then, auscultatory sounds are simultaneously output at minute sound volumes from the three respective auscultation speakers 110.

The auscultatory sounds output as sound from the auscultation speaker 110 are transmitted from the front portion 110*a* side to the cover member 130.

Further, by bringing the chest piece of the stethoscope into contact with the cover member 130, it is possible to hear the auscultatory sounds transmitted to the cover member 130.

Here, when the changeover button 152 is pressed, the sound output from the auscultation speaker 110 is switched to the sound output from the speaker 120, and it becomes possible to hear the auscultatory sound without using the stethoscope.

The auscultatory sound output as sound can be set so that a desired auscultatory sound is output via the input unit 240 of the auscultatory sound generation/management device 200. In addition, the auscultatory sound can be set so that a plurality of types of desired auscultatory sounds is output in a predetermined order. That is, a setting condition is stored in the memory 280, and the controller 220 sends the auscultatory sound information with reference thereto.

According to the above embodiment, it is possible to perform training by indirect auscultation easily using a stethoscope anytime and anywhere with a simple structure and excellent portability. Moreover, since the cover member 130 has hardness equivalent to that of human skin, it is possible to expect a training effect comparable to training which is performed by actually applying a stethoscope to a human body.

Furthermore, since the auscultation speakers 110 are provided at three locations in the auscultatory sound identification training device 100, three people can perform training by indirect auscultation at the same time, which is practical and useful.

In addition, according to the above embodiment, since auscultatory training can be performed without using a large-scale and expensive device unlike a conventional technology, handling property is excellent and there is an excellent effect that economical provision at low cost is allowed.

Further, according to the above embodiment, since a sound emitted inside is audibly checked by a hermetically sealed structure, it is possible to perform auscultatory training under an optimal environment.

Second Embodiment

Next, a second embodiment of the invention will be described below with reference to FIG. 6. The same part and/or the same function as those of the first embodiment are denoted by the same number/the same symbol, and a part of description is omitted.

Figure 6:
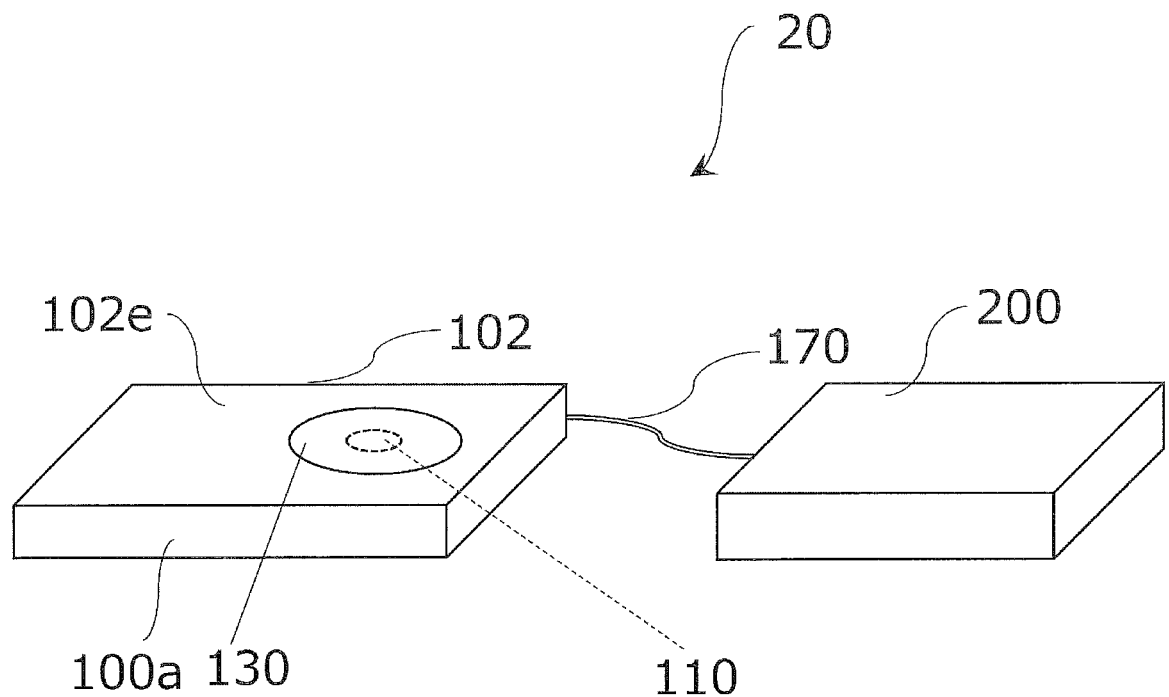
FIG. 6 is a diagram conceptually illustrating an overall configuration of an auscultatory sound identification training system according to a second embodiment of the invention.

An auscultatory sound identification training system 20 according to the present embodiment is useful for training for indirect auscultation by a stethoscope, and includes an auscultatory sound identification training device 102 and an auscultatory sound generation/management device 200 as illustrated in FIG. 6.

Figure 7:
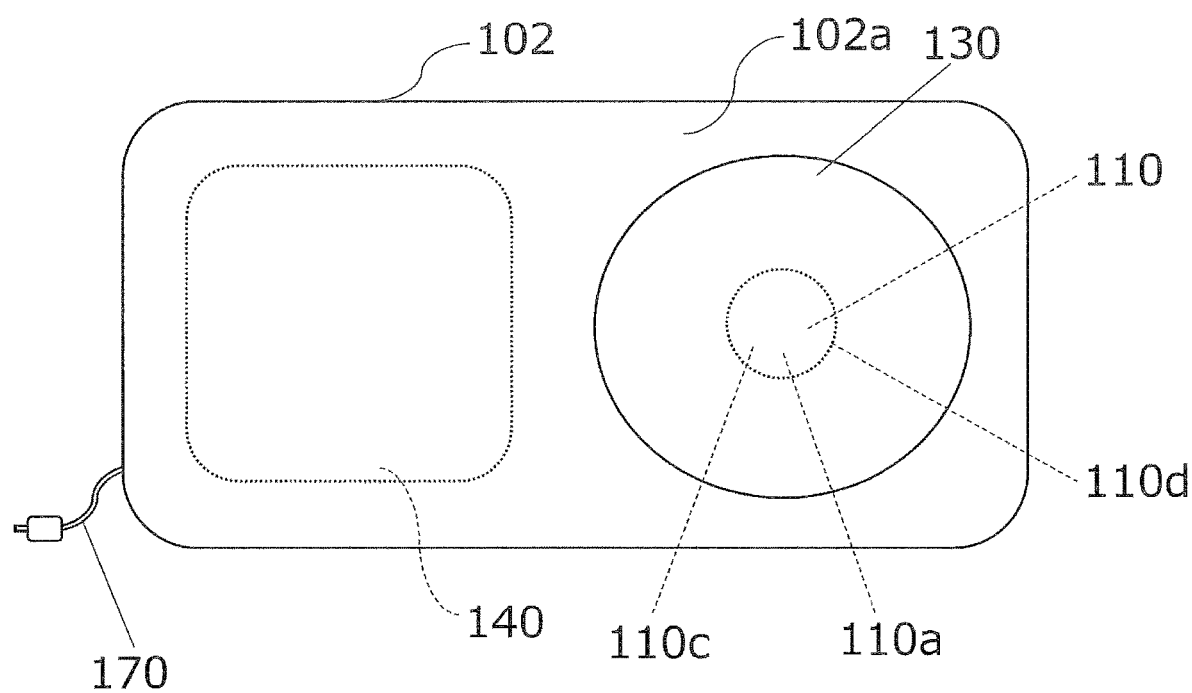
FIG. 7 is a diagram schematically illustrating an auscultatory sound identification training device according to the same embodiment.

As illustrated in FIG. 7, the auscultatory sound identification training device 102 corresponds to a hermetically sealed shape of a hollow acrylic resin rectangular parallelepiped having a width of 130 mm, a length of 80 mm, and a thickness of 15 mm, and one auscultation speaker 110 is provided in a side part (right side in FIG. 7) of the upper portion 102a. Here, a circular auscultation speaker mounting port to which the auscultation speaker 110 is fit and fixed is provided in the side part of the upper portion 102a.

When the thickness of the acrylic resin contained in the auscultatory sound identification training device 102 in the present embodiment is excessively thin, it becomes easy to resonate with internal vibration, which may cause noise. To suppress noise due to resonance, the thickness of the acrylic resin is preferably set to 3 mm or more.

In addition, it is preferable that the acrylic resin is made of a component having a sound absorbing effect and is configured so that noise from the outside of the auscultatory sound identification training device 102 is rarely transmitted to the inside thereof. Any component other than the acrylic resin can be preferably used as long as the component has such an effect.

Figure 8:
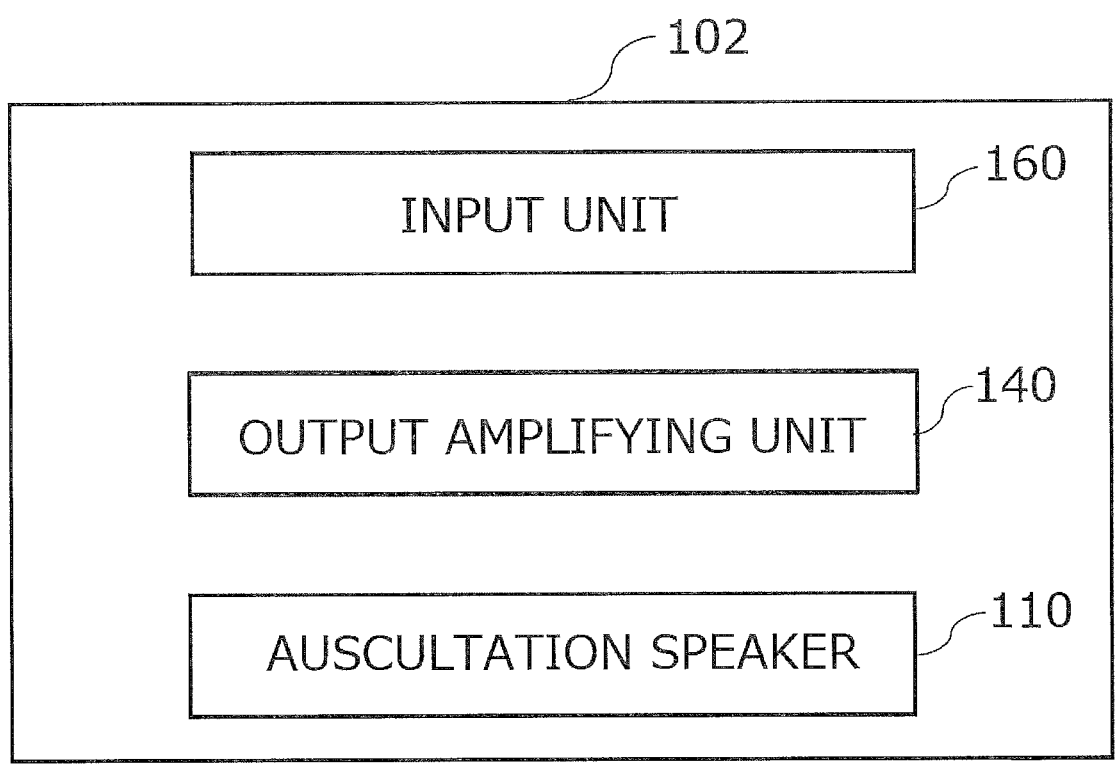
FIG. 8 is a diagram schematically illustrating a functional configuration of the auscultatory sound identification training device according to the same embodiment.

In addition, as illustrated in FIG. 8, an output amplifying unit 140, an input unit 160, and a driving battery unit (not illustrated) for supplying power to the output amplifying unit 140 are disposed in the auscultatory sound identification training device 102.

Figure 4A:
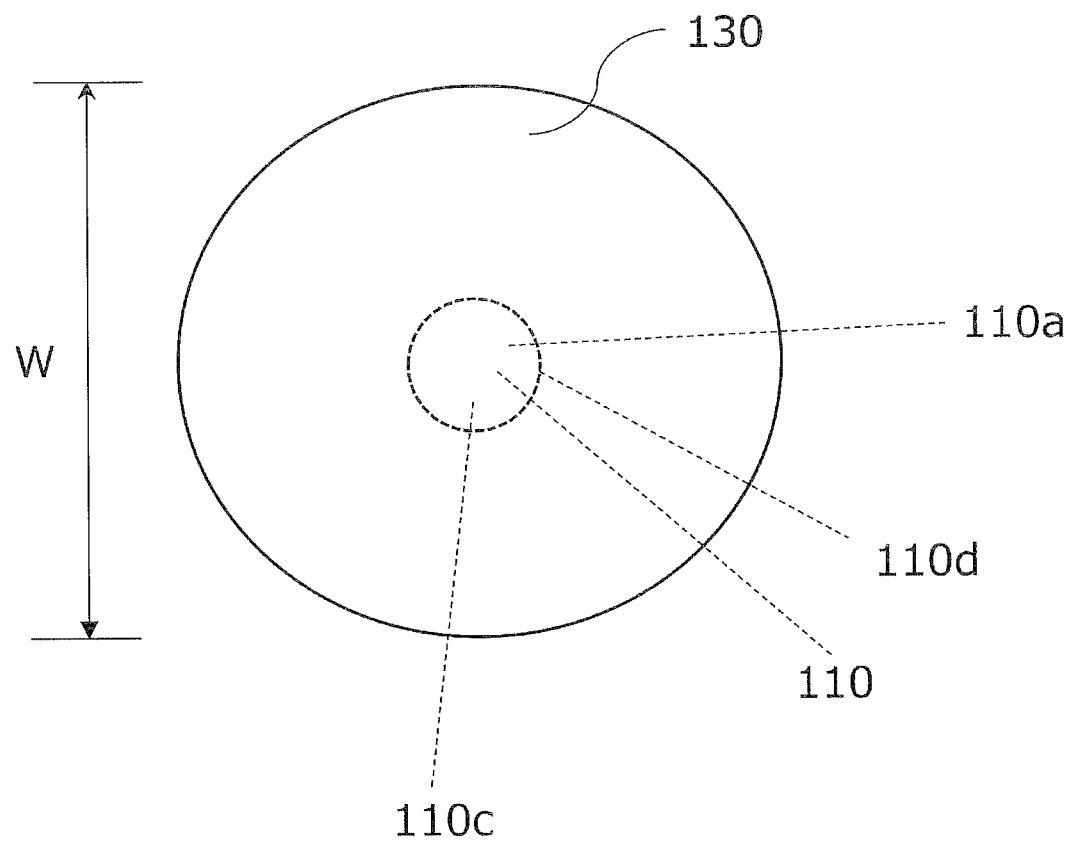
Figure 4B:
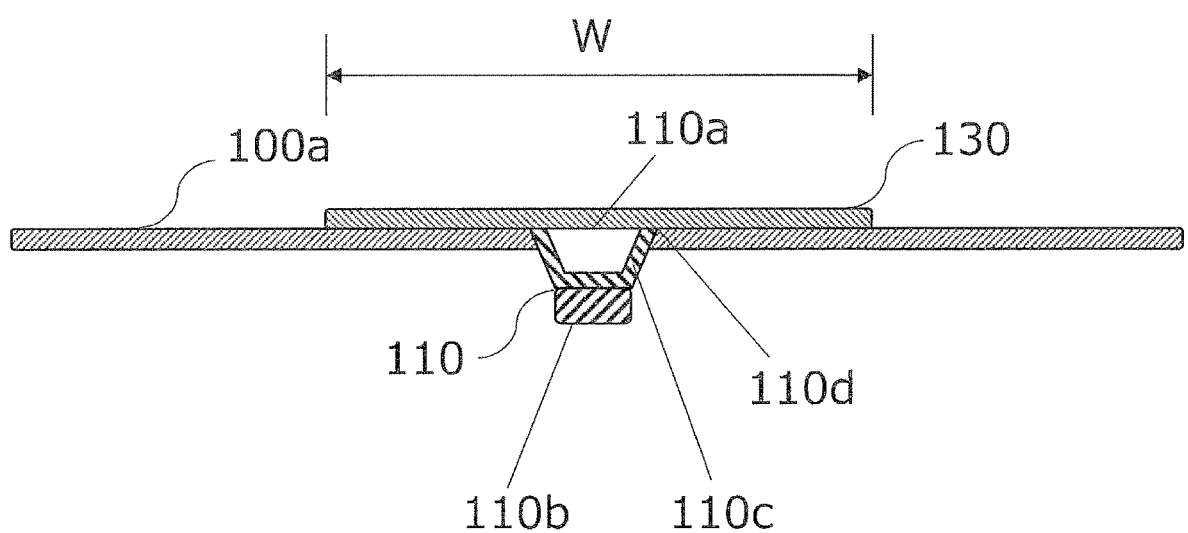

As described above, as illustrated in FIGS. 4A and 4B, the auscultation speaker 110 is a small sounding body having a circular shape on a front portion 110a side, a diameter of 22 mm, and a rated input of 0.5 watts. The auscultation speaker 110 includes a magnet and a coil located in a center part 110b and a vibrating plate (vibration member) so-called cone 110c directed outward from the center part 110b as a basic configuration, and converts a sent electric signal related to auscultatory sound information into an acoustic signal to output a sound. In addition, the auscultation speaker 110 is attached by being fit into an auscultation speaker mounting port of an upper portion 102a as a mounting plate such that an outer peripheral portion 110d on the front portion 110a side, that is, an outermost peripheral edge portion of the cone 110c is surrounded.

Further, a cover member 130 made of resin is provided on a surface portion side of the mounting plate, that is, on a surface portion side of the upper portion 102a to cover the front portion 110a side of the auscultation speaker 110. The cover member 130 has a circular shape having at least a diameter W of 45 mm and is made of a silicone resin having hardness equivalent to that of a human skin. For example, a silicone resin having low hardness (hardness is 5 to 30 degrees), preferably a silicone resin having hardness of 5 to 10 degrees is used. Here, hardness is based on JIS type A in a hardness gauge (hardness tester). In addition, considering prevention of adsorption of dust, etc. due to static electricity, a silicone resin having hardness of about 40 degrees or about 25 degrees may be used. Even though a silicone resin having a thickness of 4 mm is used, the thickness can be appropriately changed. Further, it is considered that hardness of human skin is about 5 to 10 degrees and hardness of the silicone resin is about 5 to 40 degrees as low hardness.

The diameter W of the cover member 130 is set to at least 45 mm since a width of a chest piece of a general stethoscope is 45 mm. In addition, the cover member 130 is not limited to a circular shape and may have another shape such as an elliptical shape or a quadrangular shape. However, it is necessary to configure the cover member 130 so that a shortest width (short width) of at least the cover member is 45 mm.

The output amplifying unit 140 is driven by supply of power from the battery unit and has a function of amplifying the sent electric signal related to the auscultatory sound information and outputting the amplified signal to the auscultation speaker 110.

The input unit 160 has a function of receiving an electric signal related to the auscultatory sound information sent via a connection cable 170 and sending the received electric signal to the output amplifying unit 140. In the present embodiment, inputting is performed via the connection cable 170. However, for example, wireless connection may be enabled by infrared communication or wireless communication function by Bluetooth (registered trademark).

A connecting connector is provided at one end of the connection cable 170, and the connection cable 170 is used for connection to the auscultatory sound generation/management device 200 via this connector. Further, the electric signal related to the auscultatory sound information from the auscultatory sound generation/management device 200 is sent to the input unit 160.

Figure 5:
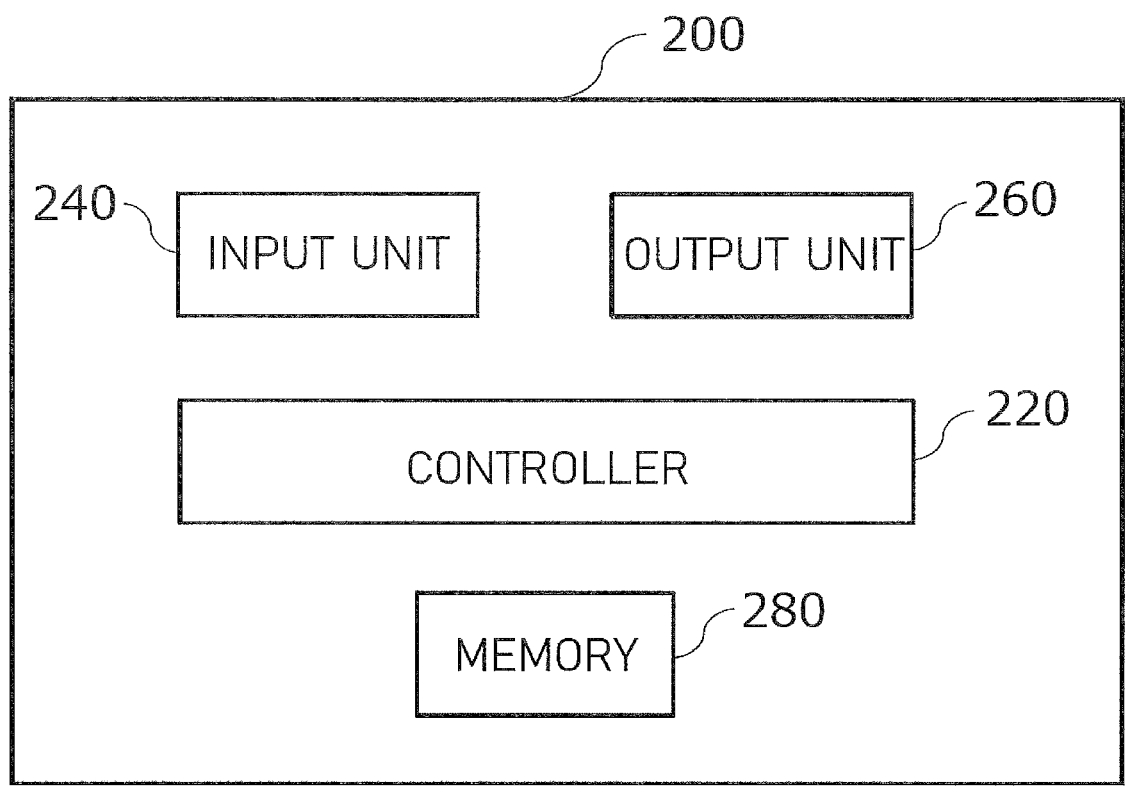
FIG. 5 is a diagram schematically illustrating a functional configuration of an auscultatory sound generation/management device according to the same embodiment.

As described above, as illustrated in FIG. 5, the auscultatory sound generation/management device 200 includes a controller 220, an input unit 240, an output unit 260, and a memory 280 disposed therein and is configured to send the electric signal related to the auscultatory sound information to the auscultatory sound identification training device 102 as described above by being connected to the auscultatory sound identification training device 102 via the connection cable 170.

The controller 220 has a function of performing a process of managing/controlling the auscultatory sound information with reference to predetermined program information stored in the memory 280. In addition, the controller 220 has a function of outputting selected auscultatory sound information via the output unit 260 based on input information of an auscultatory sound selection instruction from the input unit 240.

The input unit 240 has a function of storing input information such as an auscultatory sound or an auscultatory sound selection instruction in the memory 280 under management of the controller 220.

The output unit 260 has a function of sending the auscultatory sound information to the outside as an electric signal under management of the controller 220.

The memory 280 is a readable/writable storage device, which stores program information to be referred to by the controller 220 and stores various types of auscultatory sound information. The auscultatory sound information is stored, for example, for each age, gender, body part, degree of obesity, normal sound, and abnormal sound.

The memory 280 can add auscultatory sound to be stored through a network environment (either wireless or wired).

With regard to the above configuration, an operation will be described below.

When auscultatory sound identification training is started, an auscultatory sound of a minute volume is output from the auscultation speaker 110.

The auscultatory sound output as sound from the auscultation speaker 110 is transmitted from the front portion 110a side to the cover member 130.

Further, by bringing the chest piece of the stethoscope into contact with the cover member 130, it is possible to hear the auscultatory sounds transmitted to the cover member 130.

The auscultatory sound output as sound can be set so that a desired auscultatory sound is output via the input unit 240 of the auscultatory sound generation/management device 200. In addition, the auscultatory sound can be set so that a plurality of types of desired auscultatory sounds is output in a predetermined order. That is, a setting condition is stored in the memory 280, and the controller 220 sends the auscultatory sound information with reference thereto.

According to the above embodiment, it is possible to perform training by indirect auscultation easily using a stethoscope anytime and anywhere with a simple structure and excellent portability. Moreover, since the cover member 130 has hardness equivalent to that of human skin, it is possible to expect a training effect comparable to training which is performed by actually applying a stethoscope to a human body.

In addition, according to the above embodiment, since auscultatory training can be performed without using a large-scale and expensive device unlike a conventional technology, handling property is excellent and there is an excellent effect that economical provision at low cost is allowed.

Further, according to the above embodiment, since a sound emitted inside is audibly checked by a hermetically sealed structure, it is possible to perform auscultatory training under an optimal environment.

Figure 9:
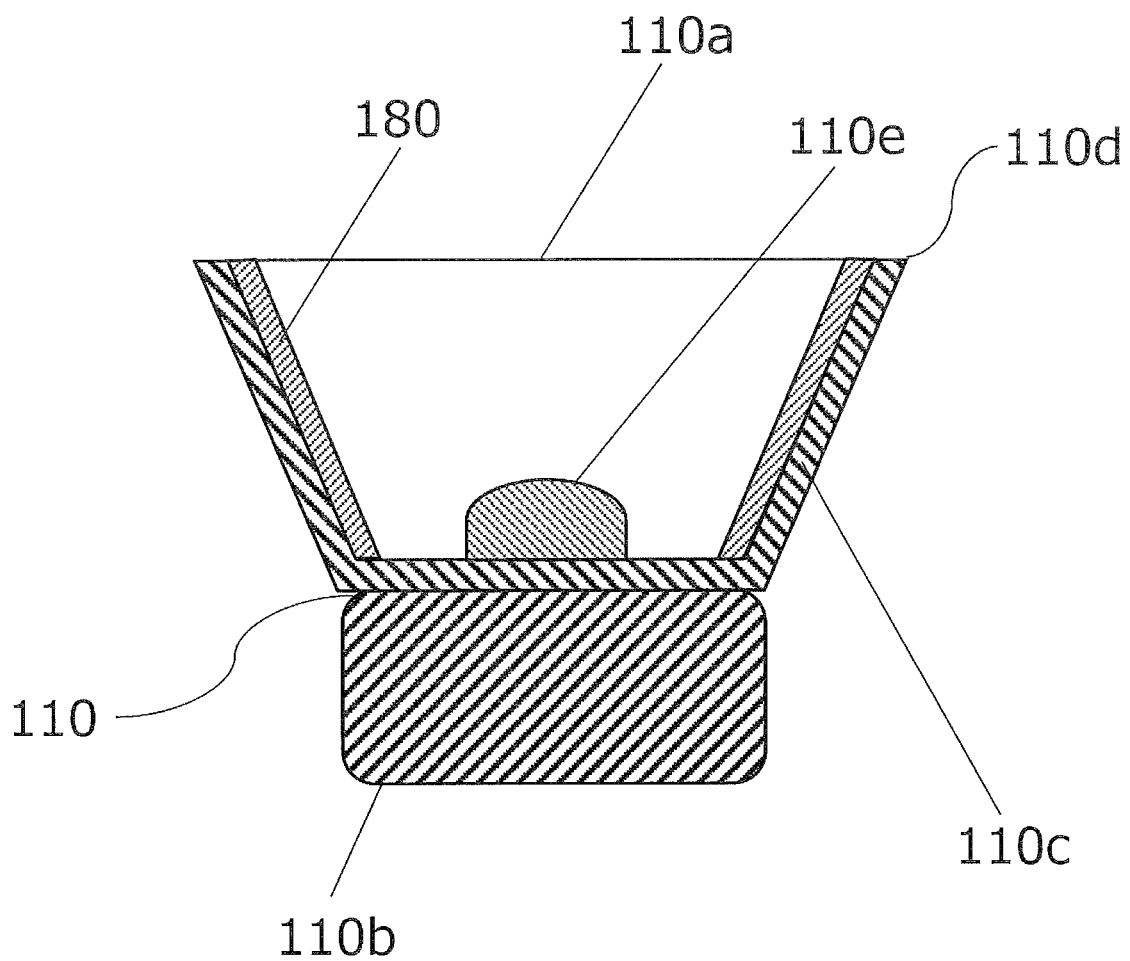
FIG. 9 is a diagram schematically illustrating a schematic configuration of an auscultation speaker of an auscultatory sound identification training device according to a modification of the same embodiment.

A modification (first modification) of the above embodiment will be described below with reference to FIG. 9. The same part and/or the same function as those of the above embodiment are denoted by the same number/the same symbol, and a part of description is omitted.

This modification is characterized by a structure of the cone 110c of the auscultation speaker 110.

The auscultation speaker 110 is a small sounding body having a circular shape on the front portion 11a side, a diameter of 22 mm, and a rated input of 0.5 watts. The auscultation speaker 110 includes a magnet and a coil located in the center part 110b, a vibrating plate (vibration member) so-called cone 110c directed outward from the center part 110b, and a center cap 110e located at an innermost peripheral portion of the cone 110c as a basic configuration, and converts a sent electric signal related to auscultatory sound information into an acoustic signal to output a sound. In addition, the auscultation speaker 110 is attached by being fit into the auscultation speaker mounting port of the upper portion 102a as a mounting plate such that the outer peripheral portion 110d on the front portion 110a side, that is, an outermost peripheral edge portion of the cone 110c is surrounded.

Further, a resin layer 180 is formed in a surface portion of the cone 110c. For example, the resin layer 180 is formed by applying a silicone resin to the entire surface of the surface portion. However, the resin layer may be formed only in a part of the surface, not the entire surface.

When the resin layer 180 is formed, depth is added to the output auscultatory sound, and it is possible to expect an effect that the auscultatory sound further approximates to an auscultatory sound generated from the human body.

Figure 10:
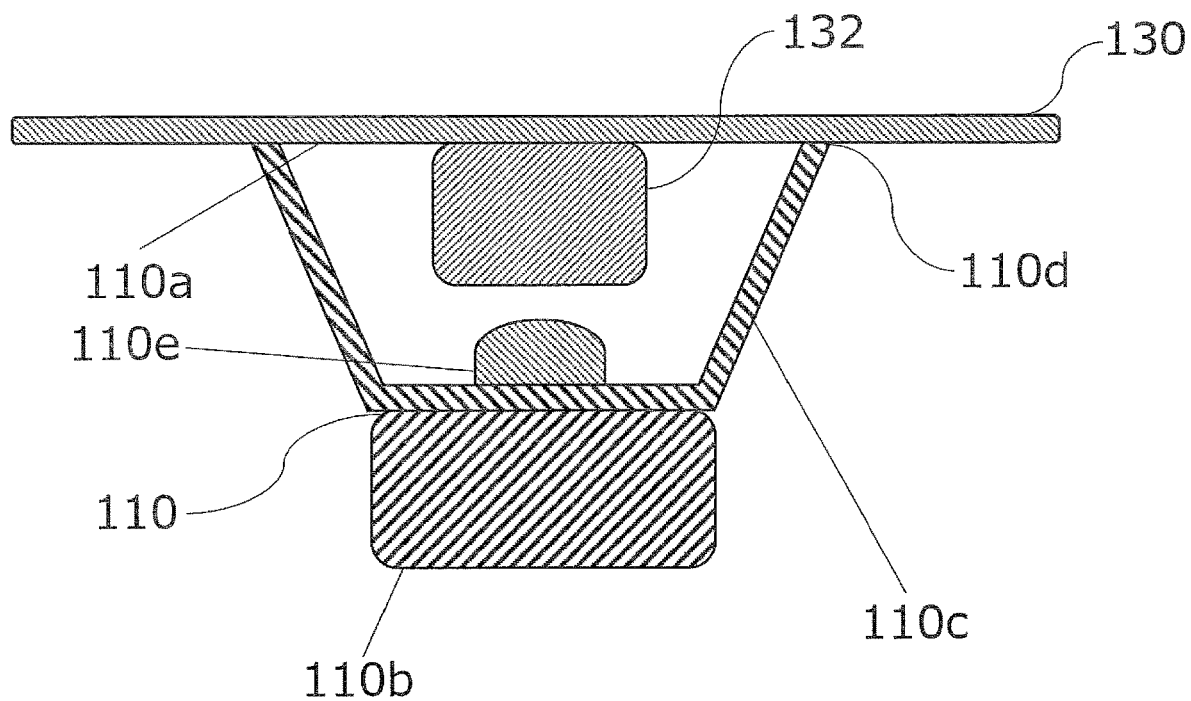
FIG. 10 is a diagram schematically illustrating a schematic configuration of an auscultation speaker and a cover member of an auscultatory sound identification training device according to another modification of the same embodiment.

Another modification (second modification) of the above embodiment will be described below with reference to FIG. 10. The same part and/or the same function as those of the above embodiment and modification are denoted by the same number/the same symbol, and a part of description is omitted.

This modification is characterized by a mounting structure of the auscultation speaker 110 and the cover member 130.

The auscultation speaker 110 is a small sounding body having a circular shape on a front portion 110a side, a diameter of 22 mm, and a rated input of 0.5 watts. The auscultation speaker 110 includes a magnet and a coil located in the center part 110b, a vibrating plate (vibration member) so-called cone 110c directed outward from the center part 110b, and the center cap 110e located at the innermost peripheral portion of the cone 110c as a basic configuration, and converts a sent electric signal related to auscultatory sound information into an acoustic signal to output a sound.

The cover member 130 made of resin is provided on the front portion 110a side of the auscultation speaker 110 to cover the front portion 110a. The cover member 130 has a circular shape having at least a diameter W of 45 mm and is made of a silicone resin having hardness equivalent to that of a human skin. For example, a silicone resin having low hardness (hardness is 5 to 30 degrees), preferably a silicone resin having hardness of 5 to 10 degrees is used as the silicone resin. Here, hardness is based on JIS type A in a hardness gauge (hardness tester). In addition, considering prevention of adsorption of dust, etc. due to static electricity, a silicone resin having hardness of about 40 degrees or about 25 degrees may be used. Even though a silicone resin having a thickness of 4 mm is used, the thickness can be appropriately changed. Further, it is considered that hardness of human skin is about 5 to 10 degrees and hardness of the silicone resin is about 5 to 40 degrees as low hardness.

The diameter W of the cover member 130 is set to at least 45 mm since a width of a chest piece of a general stethoscope is 45 mm. In addition, the cover member 130 is not limited to a circular shape and may have another shape such as an elliptical shape or a quadrangular shape. However, it is necessary to configure the cover member 130 so that a shortest width (short width) of at least the cover member is 45 mm.

In addition, a rectangular parallelepiped-shaped conductive member 132 is provided in the center part of the cover member 130 such that the member is directed toward the center cap 110*e*. The conductive member 132 is made of, for example, silicone resin.

Further, when the stethoscope comes into contact with the cover member 130, the cover member 130 is pushed and bent. In conjunction therewith, the conductive member 132 moves and abuts on the center cap 110*e*, and auscultatory sound is transmitted.

Figure 11:
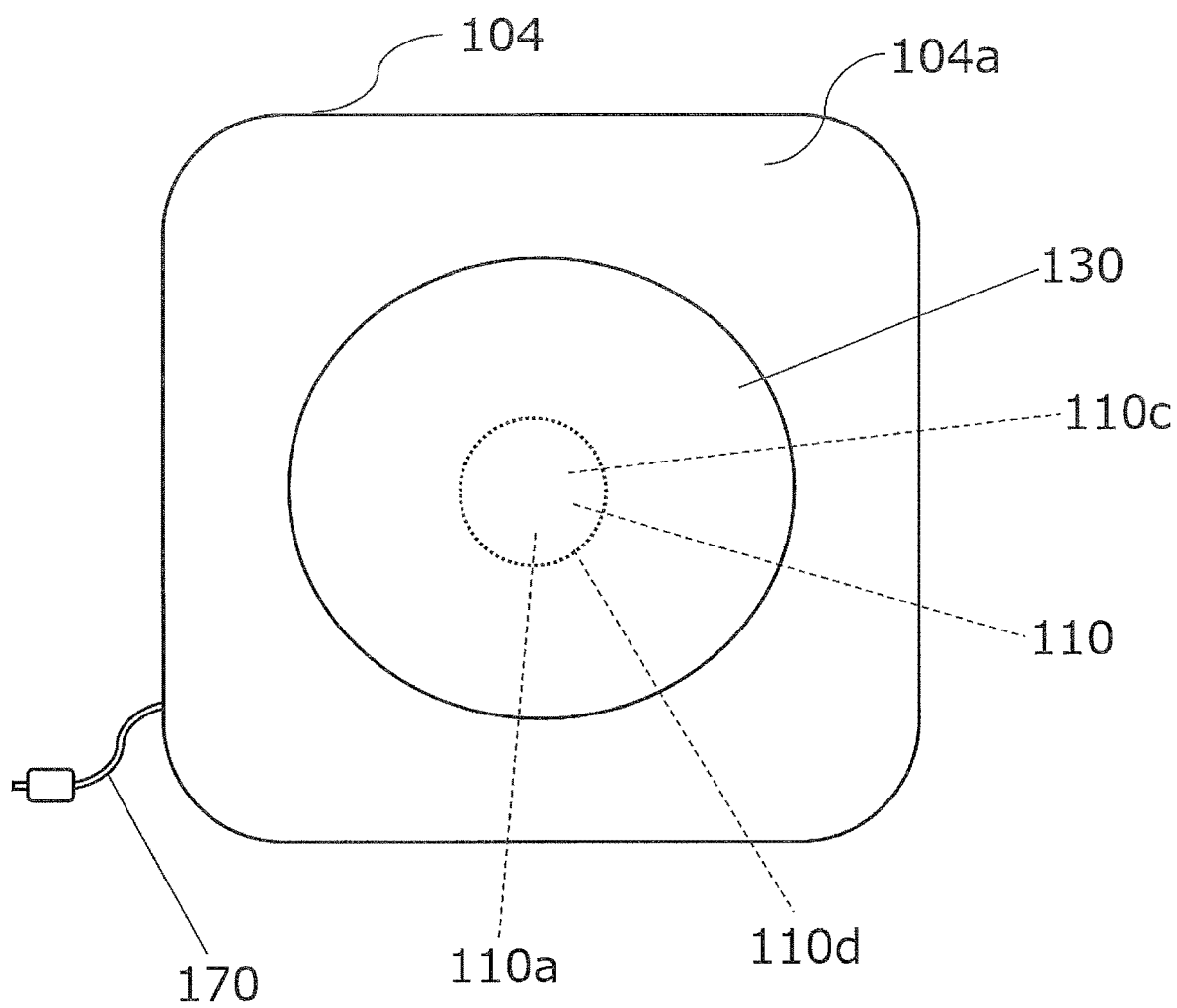
FIG. 11 is a diagram schematically illustrating an auscultatory sound identification training device according to still another modification of the same embodiment.

Still another modification (third modification) of the above embodiment will be mainly described below with reference to FIG. 11. The same part and/or the same function as those of the above embodiment and modifications are denoted by the same number/the same symbol, and a part of description is omitted.

This modification is characterized by a structure of the auscultatory sound identification training device.

An auscultatory sound identification training device 104 corresponds to a hollow rectangular parallelepiped which has a width of 80 mm, a length of 80 mm, and a thickness of 15 mm, is made of an acrylic resin, and has a hermetically sealed structure, and one auscultation speaker 110 is provided on an upper portion 104*a*. Here, a circular auscultation speaker mounting port to which an auscultation speaker 110 is fit and fixed is provided on the upper portion 104*a*.

When the thickness of the acrylic resin contained in the auscultatory sound identification training device 104 in the present modification is excessively thin, it becomes easy to resonate with internal vibration, which may cause noise. To suppress noise due to resonance, the thickness of the acrylic resin is preferably set to 3 mm or more.

In addition, it is preferable that the acrylic resin is made of a component having a sound absorbing effect and is configured so that noise from the outside of the auscultatory sound identification training device 104 is rarely transmitted to the inside thereof. Any component other than the acrylic resin can be preferably used as long as the component has such an effect.

In addition, the auscultatory sound identification training device 104 has an input unit (not illustrated) disposed therein, and has a connection cable 170.

The auscultation speaker 110 is a small sounding body having a circular shape on a front portion 110*a* side, a diameter of 22 mm, and a rated input of 0.5 watts. The auscultation speaker 110 includes a magnet and a coil located in a center part 110*b* and a vibrating plate (vibration member) so-called cone 110*c* directed outward from the center part 110*b* as a basic configuration, and converts a sent electric signal related to auscultatory sound information into an acoustic signal to output a sound. In addition, the auscultation speaker 110 is attached by being fit into an auscultation speaker mounting port of the upper portion 104*a* as a mounting plate such that an outer peripheral portion 110*d* on the front portion 110*a* side, that is, an outermost peripheral edge portion of the cone 110*c* is surrounded.

Further, a cover member 130 made of resin is provided on a surface portion side of the mounting plate, that is, on a surface portion side of the upper portion 104*a* to cover the front portion 110*a* side of the auscultation speaker 110. The cover member 130 has a circular shape having at least a diameter W of 45 mm and has hardness equivalent to that of a human skin. For example, a silicone resin having low hardness (hardness is 5 to 30 degrees), preferably a silicone resin having hardness of 5 to 10 degrees is used. Here, hardness is based on JIS type A in a hardness gauge (hardness tester). In addition, considering prevention of adsorption of dust, etc. due to static electricity, a silicone resin having hardness of about 40 degrees or about 25 degrees may be used. Even though a silicone resin having a thickness of 4 mm is used, the thickness can be appropriately changed. Further, it is considered that hardness of human skin is about 5 to 10 degrees and hardness of the silicone resin is about 5 to 40 degrees as low hardness.

The diameter W of the cover member 130 is set to at least 45 mm since a width of a chest piece of a general stethoscope is 45 mm. In addition, the cover member 130 is not limited to a circular shape and may have another shape such as an elliptical shape or a quadrangular shape. However, it is necessary to configure the cover member 130 so that a shortest width (short width) of at least the cover member is 45 mm.

The input unit has a function of receiving an electric signal related to auscultatory sound information sent via the connection cable 170 and sending the received electric signal to the auscultation speaker 110.

A connecting connector is provided at one end of the connection cable 170, and the connection cable 170 is used for connection to the auscultatory sound generation/management device 200 via this connector. Further, the electric signal related to the auscultatory sound information from the auscultatory sound generation/management device 200 is sent to the input unit.

With regard to such a configuration, an operation will be described below.

When auscultatory sound identification training is started, an auscultatory sound of a minute volume is output from the auscultation speaker 110.

The auscultatory sound output as sound from the auscultation speaker 110 is transmitted from the front portion 110*a* side to the cover member 130.

Further, by bringing the chest piece of the stethoscope into contact with the cover member 130, it is possible to hear the auscultatory sounds transmitted to the cover member 130.

The auscultatory sound output as sound can be set so that a desired auscultatory sound is output via the input unit 240 of the auscultatory sound generation/management device 200. In addition, the auscultatory sound can be set so that a plurality of types of desired auscultatory sounds is output in a predetermined order. That is, a setting condition is stored in the memory 280, and the controller 220 sends the auscultatory sound information with reference thereto.

According to the above modification, it is possible to perform training by indirect auscultation easily using a stethoscope anytime and anywhere with a simple structure and excellent portability. Moreover, since the cover member 130 has hardness equivalent to that of human skin, it is possible to expect a training effect comparable to training which is performed by actually applying a stethoscope to a human body.

In addition, according to the above embodiment, since auscultatory training can be performed without using a large-scale and expensive device unlike a conventional technology, handling property is excellent and there is an excellent effect that economical provision at low cost is allowed.

Further, according to the above embodiment, since a sound emitted inside is audibly checked by a hermetically sealed structure, it is possible to perform auscultatory training under an optimal environment.

Third Embodiment

Next, a third embodiment of the invention will be described below with reference to FIG. 12 to FIG. 15C. The same part and/or the same function as those of the first and second embodiments are denoted by the same number/the same symbol, and a part of description is omitted.

Figure 12:
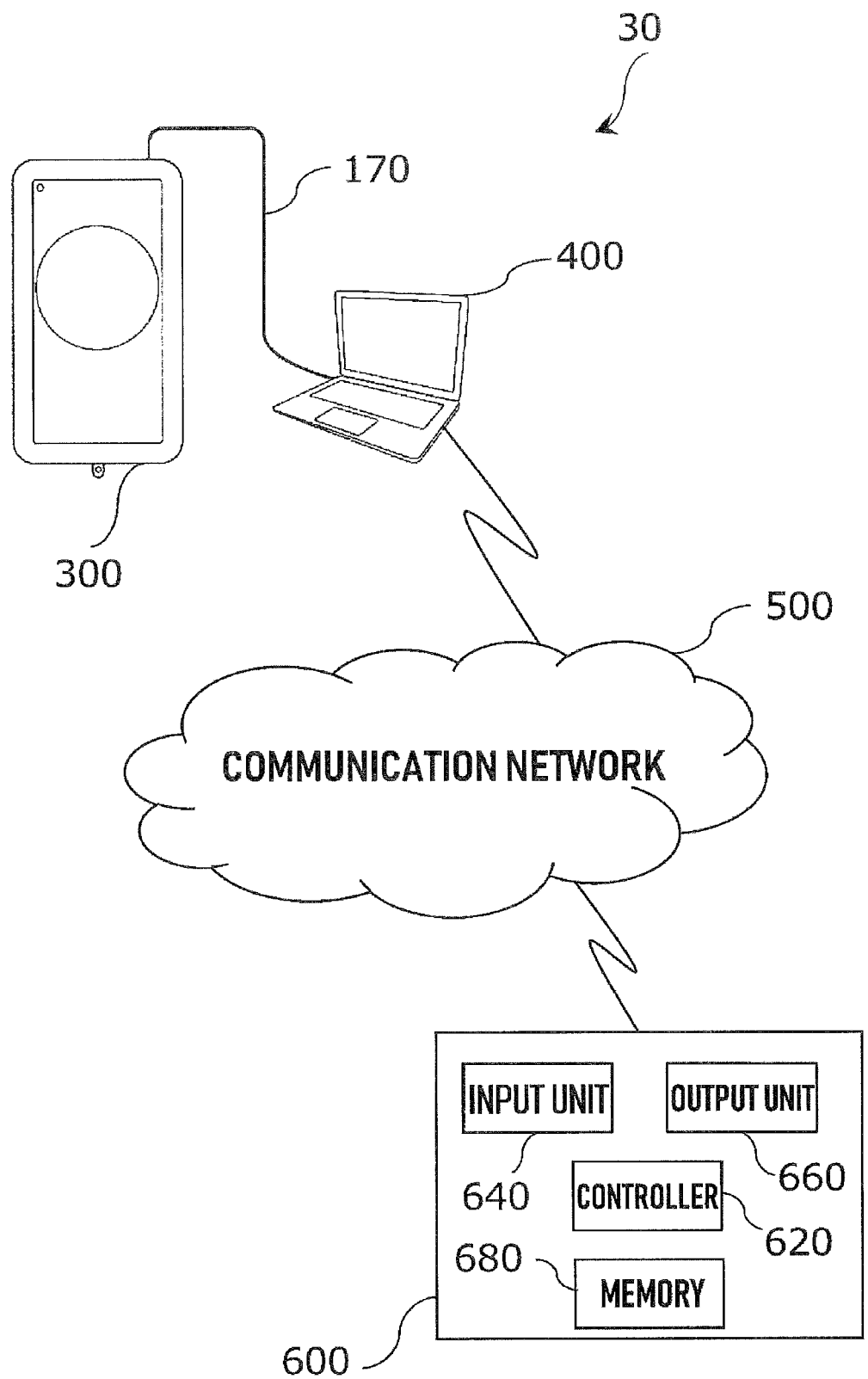
FIG. 12 is a diagram schematically illustrating an overall configuration of an auscultatory sound identification training system according to a third embodiment of the invention.

An auscultatory sound identification training system 30 according to the present embodiment makes it possible to realize training for indirect auscultation by a stethoscope under a network environment. As illustrated in FIG. 12, the system includes a personal computer (PC) 400 having a web browser function in which an auscultatory sound identification training device 300 is connected via a connection cable 170, and a cloud server computer (server) 600 connected to the PC 400 via a communication network 500. For communication between the PC 400 and the server 600 via the communication network 500, transmission and reception of information is performed by IETF TLS communication (for example, SSL communication) as a security measure.

Even though the PC 400 is used in the present embodiment, the invention is not limited thereto. For example, it is possible to use a terminal device having a web browser function such as a tablet type terminal device or a smartphone.

Figure 13:
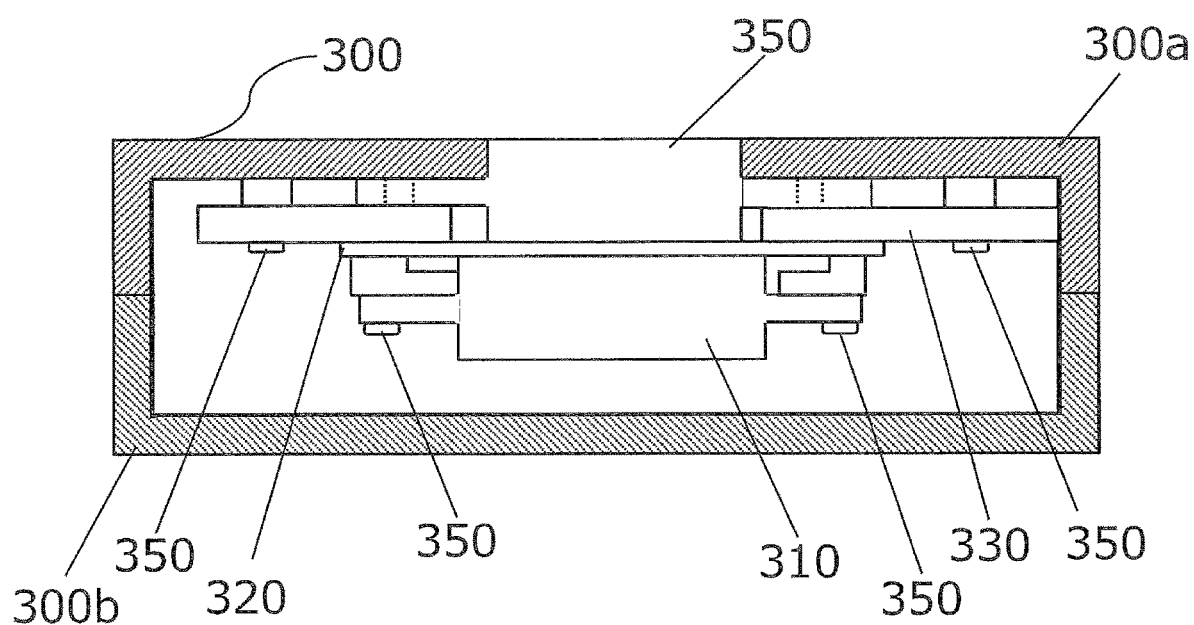
FIG. 13 is a diagram schematically illustrating a positional relationship between an auscultation speaker, a vibrating plate, and a cover in an auscultatory sound identification training device from a side according to the same embodiment.

The auscultatory sound identification training device 300 corresponds to a hollow hermetically sealed rectangular parallelepiped made of an acrylic resin having a width of 76 mm, a length of 135 mm, and a thickness of 35 mm and includes an upper case 300a and a lower case 300b, and an auscultation speaker 310 is provided on a surface portion side (upper case 300a side) thereof. The auscultation speaker 310 is an exciter type speaker, is capable of generating sound using a contact object as a vibrating plate (vibration member), and has a characteristic of being strong against heavy bass. In the present embodiment, as illustrated in FIG. 13, a vibrating plate 320 is provided on a front surface side of the auscultation speaker 310 (an upper side of the speaker 310 in FIG. 13) in a state of surface contact.

When thicknesses of the upper case 300a and the lower case 300b in the present embodiment are excessively thin, it becomes easy to resonate with internal vibration, which may cause noise. To suppress noise due to resonance, the thicknesses are preferably set to 3 mm or more.

In addition, it is preferable that the upper case 300a and the lower case 300b are made of an acrylic resin component having a sound absorbing effect and are configured so that noise from the outside of the auscultatory sound identification training device 300 is rarely transmitted to the inside thereof. Any component other than the acrylic resin can be preferably used as long as the component has such an effect.

That is, the auscultation speaker 310 and the vibrating plate 320 are attached so as to be attachable and detachable via a screw 340 in such a manner as to be suspended from a resin plate 330 provided in the upper case 300a.

In addition, a lower portion of a circular cover member 350 made of a silicone resin is provided on an upper portion of the vibrating plate 320 in a state of surface contact with the vibrating plate 320. The upper portion of the cover member 350 is fit into a circular hole portion provided in the upper case 300a and is flush with the upper portion of the upper case 300a (that is, the auscultatory sound identification training device 300 and the surface portion). A diameter W of the hole portion is preferably at least 45 mm since a width of a chest piece of a general stethoscope is 45 mm. The hole portion is not limited to a circular shape and may have another shape such as an elliptical shape or a quadrangular shape. However, it is preferable to configure the hole portion so that at least a shortest width (short width) is 45 mm.

Here, a silicone resin having a hardness of 40 degrees is used. In addition, sizes of a vertical width and a horizontal width of the vibrating plate 320 are larger than vertical widths and horizontal widths of the cover member 330 and the auscultation speaker 310. Here, hardness is based on JIS type A in a hardness gauge (hardness tester). A silicone resin having low hardness (hardness is 5 to 30 degrees), preferably a silicone resin having hardness of 5 to 10 degrees is preferably used. However, considering prevention of adsorption of dust, etc. due to static electricity, a silicone resin having hardness of about 40 degrees or about 25 degrees may be used. Even though a silicone resin having a thickness of 4 mm is used, the thickness can be appropriately changed. Further, it is considered that hardness of human skin is about 5 to 10 degrees and hardness of the silicone resin is about 5 to 40 degrees as low hardness. In addition, the silicone resin is white. Since it becomes easy to make dirt conspicuous using white, it is possible to expect an effect of not transferring dirt to the stethoscope.

Further, the circular cover member 330 made of a silicone resin is provided on the surface portion side of the auscultatory sound identification training device 300 to cover the front surface side of the auscultation speaker 310 in a state of surface contact with the vibrating plate 320.

Figure 14:
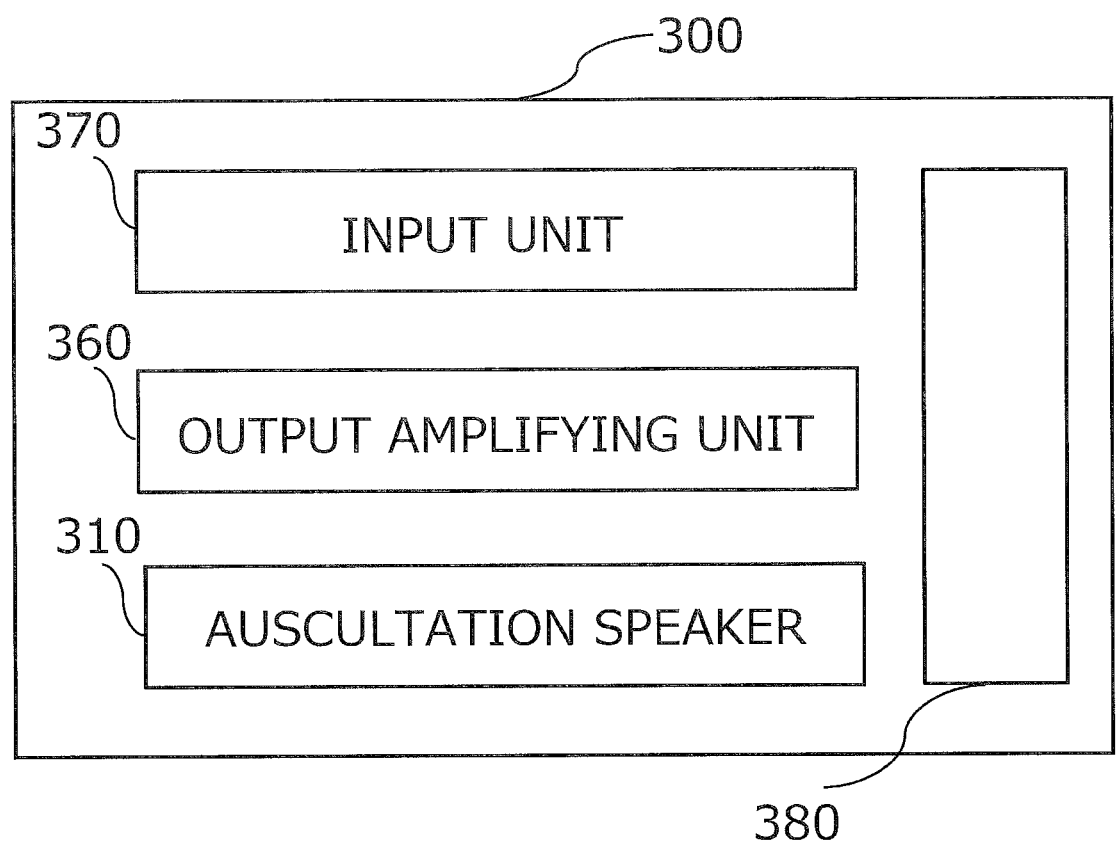
FIG. 14 is a diagram schematically illustrating a functional configuration of the auscultatory sound identification training device according to the same embodiment.

In addition, as illustrated in FIG. 14, an output amplifying unit 360 having an output adjustment function, an input unit 370 having a function of receiving an audio signal sent from the outside and sending the signal to the output amplifying unit 360, and a battery unit 380 for supplying driving power to the output amplifying unit 360 are disposed in the auscultatory sound identification training device 300.

Figure 15A:
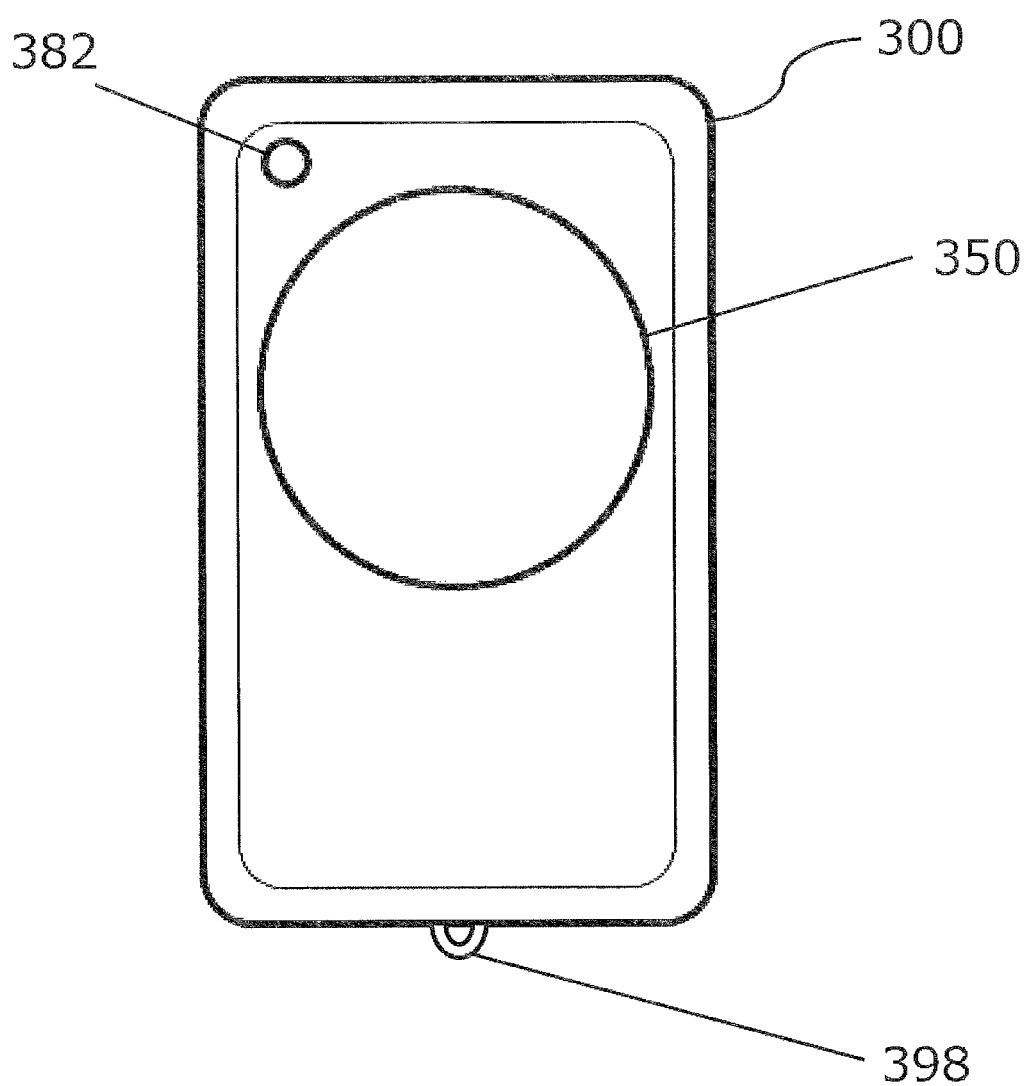

As illustrated in FIG. 15A, a light emitting diode (LED) indication lamp 382 connected to the battery 380 and capable of visually recognizing ON/OFF states of a power supply is provided on the surface portion side of the auscultatory sound identification training device 300. In the LED indication lamp 382, an LED is lit up when the power supply is turned ON.

Figure 15B:
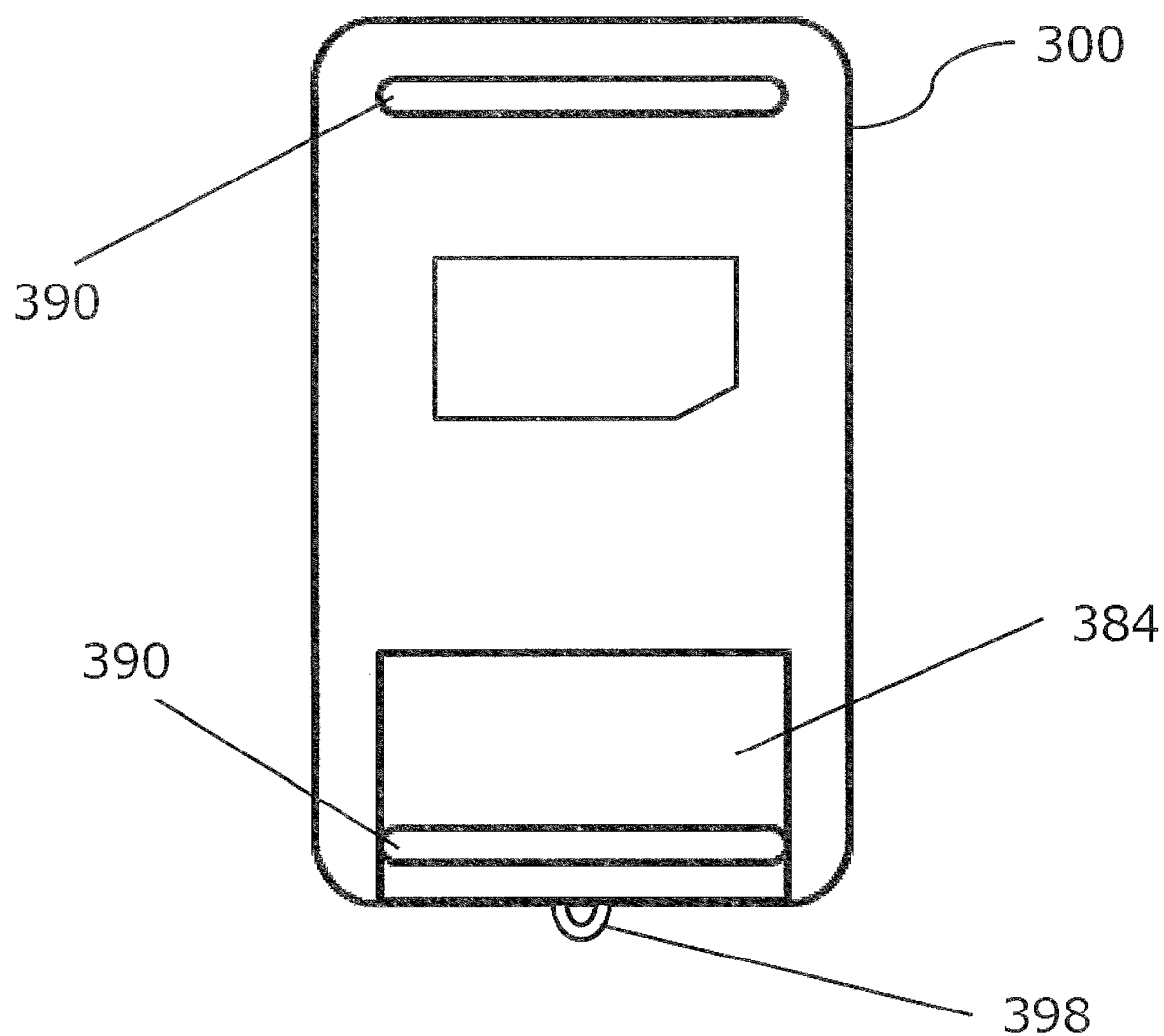

In addition, as illustrated in FIG. 15B, one soundproof/vibration isolating member (elastic member) 390 is provided in each of an upper part and a lower part on a back surface side of the auscultatory sound identification training device 300. For example, when the auscultatory sound identification training device 300 is placed on a desk and used, the soundproof/vibration isolating member 390 functions not to pick up noise and vibration from the desk and functions as a slip prevention. Here, the soundproof/vibration isolating member 390 provided in the lower part is provided on a storage case cover 384 of a battery storage case for detachably storing the battery 380 therein.

Figure 15C:
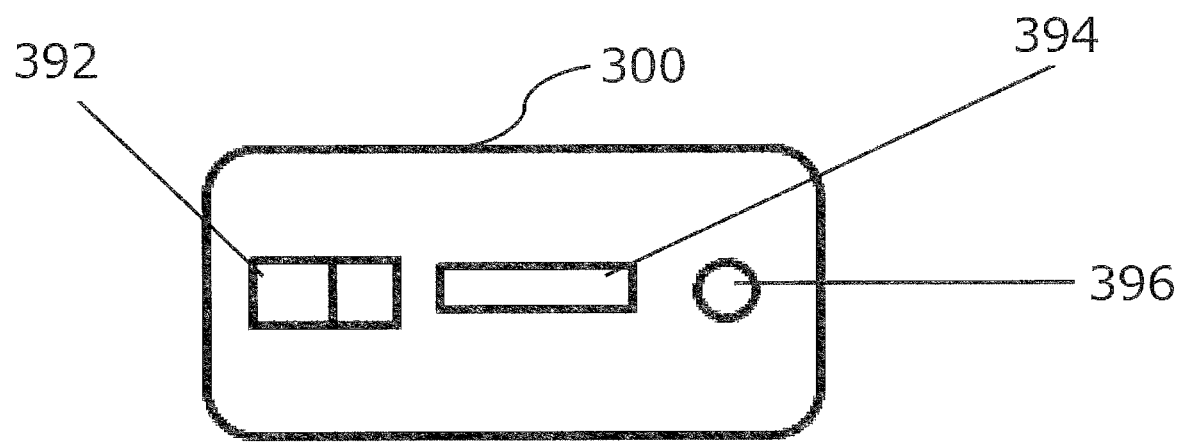

Further, as illustrated in FIG. 15C, a power switch 392, a volume adjustment knob 394, and an input terminal portion 396 are provided on the upper portion side of the auscultatory sound identification training device 300.

The power switch 392 is connected to the battery 380 and the LED indication lamp 382 to turn ON/OFF the power supply. The LED indication lamp 382 is turned ON when the power supply is in an ON state, and the LED indication lamp 382 is turned OFF when the power supply is in an OFF state.

The volume adjustment knob 394 is connected to the output amplifying unit 360 and has a function of sound volume adjustment. For example, the sound volume is increased when a dial is turned to the left as seen from an upper surface and is decreased when the dial is turned to the right.

The input terminal portion 396 is a terminal which is connected to the input unit 370 and to which the connection cable 170 for connection to the PC 400 is detachably mounted.

Further, for example, a strap hook 398 for attaching a neck strap is provided on the bottom portion side of the auscultatory sound identification training device 300.

As illustrated in FIG. 12, the server 600 includes a controller 620, an input unit 640, an output unit 660, and a memory 680 disposed therein, and is configured to send an electric signal related to auscultatory sound information by being connected to the PC 400 accessed via the communication network 500.

The controller 620 has a function of performing a process of managing/controlling the auscultatory sound information with reference to predetermined program information stored in the memory 680. In addition, the controller 620 has a function of outputting selected auscultatory sound information via the output unit 660 based on input information of an auscultatory sound selection instruction from the input unit 640.

The input unit 640 has a function of storing input information such as an auscultatory sound or an auscultatory sound selection instruction in the memory 680 under management of the controller 620.

The output unit 660 has a function of sending the auscultatory sound information to the outside as an electric signal under management of the controller 620.

The memory 680 is a readable/writable storage device, which stores program information to be referred to by the controller 620 and stores various types of auscultatory sound information. The auscultatory sound information is stored, for example, for each age, gender, body part, degree of obesity, normal sound, and abnormal sound in a table form.

The auscultatory sound information is biological sound information of 20 Hz to 700 Hz, and stores, for example, normal heart sound information as bass information considering a frequency band of a biological sound for each age, gender, body part, and degree of obesity.

With regard to the above configuration, an operation will be described below.

When the auscultatory sound identification training device 300 is connected to the PC 400 via the connection cable 170, and the PC 400 accesses the server 600 via the communication network 500, auscultatory sound identification training is started. Then, an auscultatory sound of a minute sound volume is output from the auscultation speaker 610.

The auscultatory sound output from the auscultation speaker 610 as sound is directly transmitted to the vibrating plate 320 without passing through a space from the front portion side.

Further, when a chest piece of a stethoscope is brought into contact with the cover member 350, the auscultatory sound directly transmitted to the vibrating plate 320 is transmitted to the cover member 350 without passing through the space, and thus the auscultatory sound can be heard.

The auscultatory sound output as sound can be set so that a desired auscultatory sound stored in the memory 680 is output with reference to instruction information from the PC 400 to the server 600. In addition, the auscultatory sound can be set so that a plurality of types of desired auscultatory sounds is output in a predetermined order. That is, a setting condition is stored in the memory 680, and the controller 620 sends the auscultatory sound information with reference thereto.

According to the above embodiment, it is possible to perform training by indirect auscultation easily using a stethoscope anytime and anywhere with a simple structure and excellent portability. Moreover, since the auscultatory sound is directly transmitted from the auscultation speaker 310 to the vibrating plate 320 and from the vibrating plate 320 to the cover member 350 without passing through a space, it is possible to expect a training effect comparable to training which is performed by actually applying a stethoscope to a human body.

In addition, for example, since it is difficult to determine whether abnormal pattern of heart sound (so-called systolic murmur) that sounds when the heart contracts corresponds to a systole phase or a diastolic phase only by listening to the auscultatory sound, a trainee is instructed to perform auscultation while taking pulse in a clinical practice. According to the above embodiment, since the auscultatory sound is directly transmitted, the cover member 350 can be palpated so as to hit a pulse. In this way, it is possible to expect an effect that auscultation is performed while taking this pulse.

Further, since the auscultation speaker 310 is provided on the upper case 300a side, for example, it is possible to prevent the auscultatory sound from being transmitted to the desk on which the auscultatory sound identification training device 300 is placed.

In addition, according to the above embodiment, since auscultatory training can be performed without using a large-scale and expensive device unlike a conventional technology, handling property is excellent and there is an excellent effect that economical provision at low cost is allowed.

In addition, according to the above embodiment, remote auscultation is feasible, auscultatory training can be performed anytime and anywhere, and it becomes practical and useful.

Furthermore, according to the above embodiment, the soundproof/vibration isolating member 390 makes it difficult to transmit noise from the outside, sound emitted inside can be directly heard using a stethoscope by a hermetically sealed structure, and thus it is possible to perform auscultatory training under an optimum environment.

Incidentally, since the strap hook 398 is provided in the auscultatory sound identification training device 300, when the auscultatory sound identification training device 300 is adjusted to be located around, for example, a chest of a human body at the time of hanging the neck strap attached to the strap hook 398 around a neck, it is applicable to auscultatory training for a simulated patient in clinical education. That is, since the cover member 350 is positioned around the chest, it is possible to perform auscultatory training for heart sound and lung sound.

In medical education, it is a general scheme to conduct clinical education using a simulator or a simulated patient (for example, a volunteer), and heart sound and lung sound of a simulated patient playing a role of a sick person saying "painful" in words, etc. are normal. Thus, sense of reality is impaired. Here, it is possible to obtain sense of presence by auscultating abnormal sound corresponding to a disease name using the auscultatory sound identification training device 300 attached to the neck strap.

The sounding body is not limited to the above embodiment. For example, it is possible to use a piezoelectric type speaker.

Figure 16:
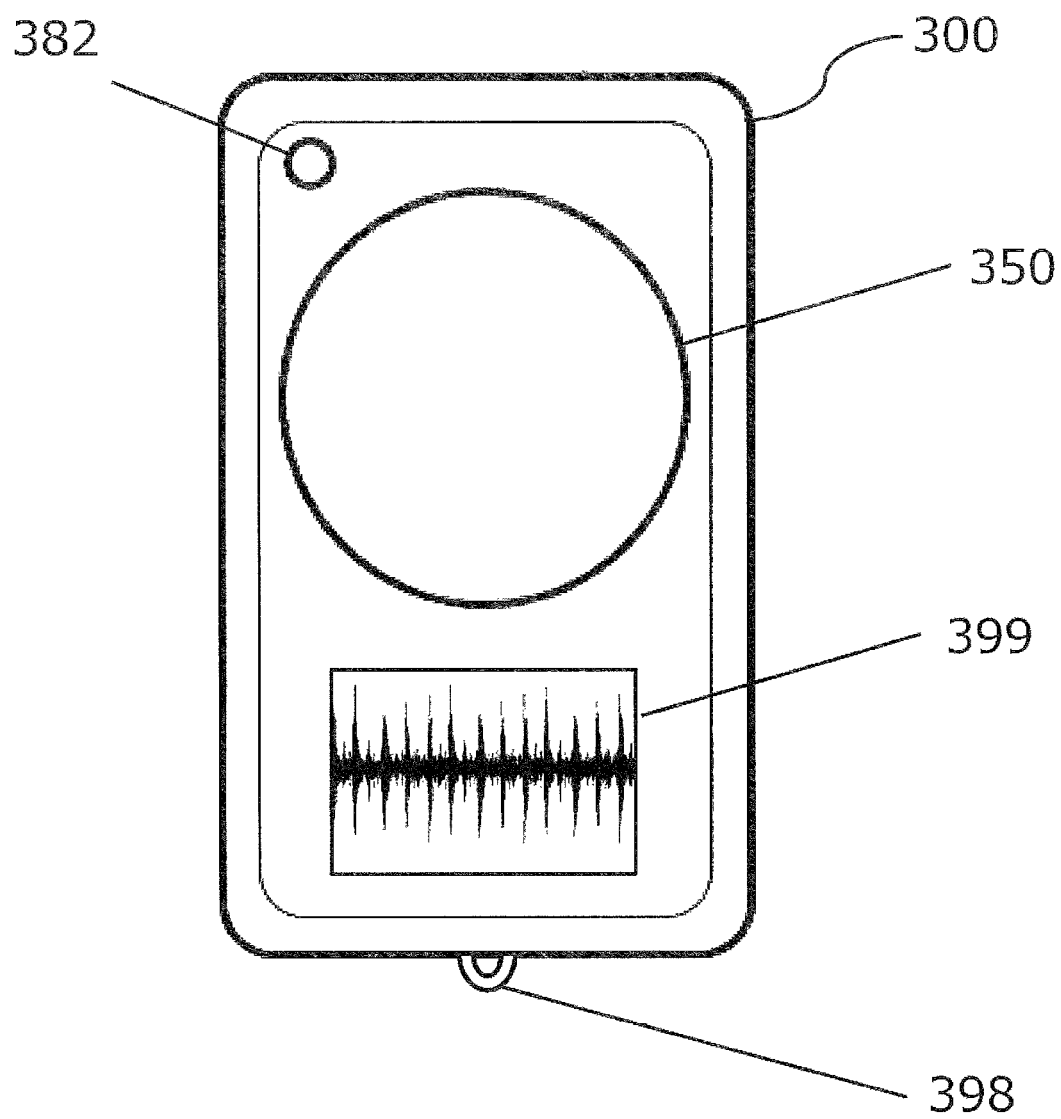
FIG. 16 is a diagram schematically illustrating an appearance of an auscultatory sound identification training device having a liquid crystal monitor waveform display function according to a modification of the same embodiment.

In addition, FIG. 16 illustrates a modification of the present embodiment. The same part and/or the same function as those of the above embodiment are denoted by the same number/the same symbol, and a description is omitted. In this modification, a waveform of a heart sound or a lung sound can be output and displayed on a liquid crystal monitor 399. In this way, it can be expected to increase accuracy of auscultatory training and further enhance the learning effect.

Figure 17:
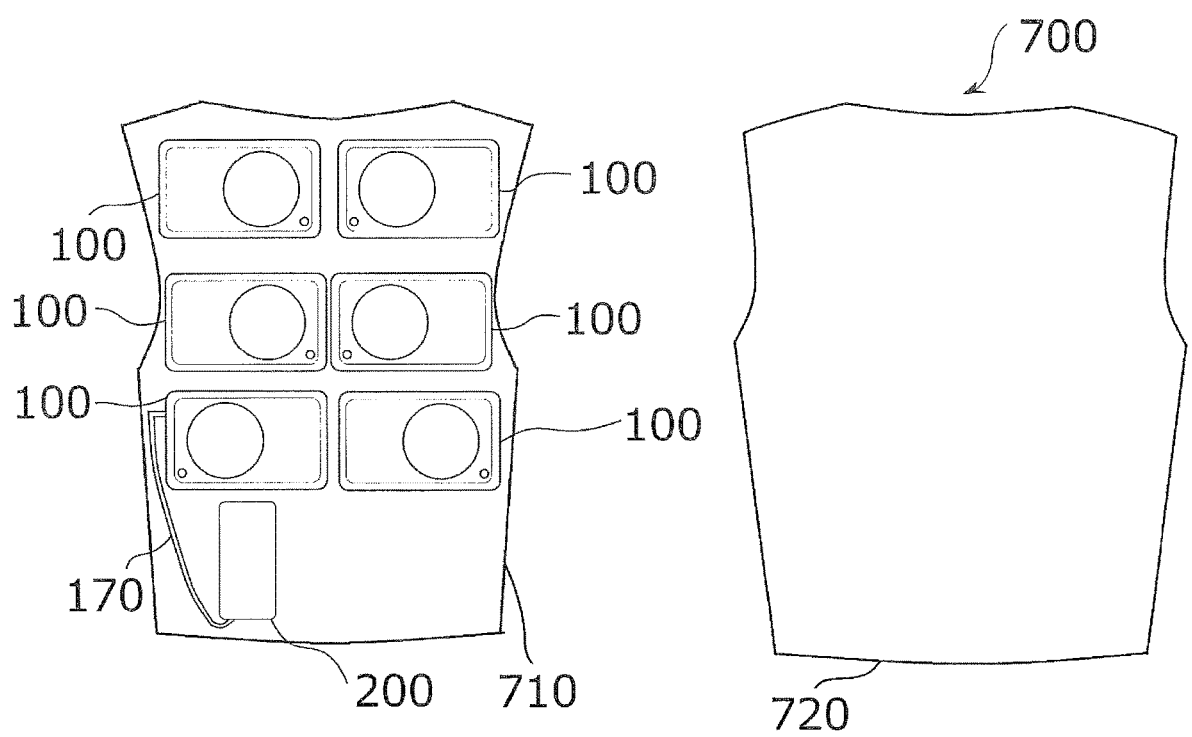
FIG. 17 is a schematic view of an auscultation vest (outer and inner) using the auscultatory sound identification training device according to the second embodiment of the invention as seen from a front.

FIG. 17 illustrates an example of an auscultation vest using the auscultatory sound identification training device according to the embodiment of the present invention. An auscultation vest 700 includes an inner 710 and an outer 720.

The inner 710 is provided with an installation portion (not illustrated) allowing detachable installation of one or more auscultatory sound identification training devices 100 and auscultatory sound generation/management devices 200. For example, any installation portion such as a tape, a magic tape, or a pocket may be used as this installation portion as long as the auscultatory sound identification training device 100 and the auscultatory sound generation/management device 200 can be detachably installed. When the magic tape is used as the installation portion, a male surface or a female surface is provided to the inner 710, and a corresponding surface is provided on a rear side of the auscultatory sound identification training device 100 and the auscultatory sound generation/management device 200. In addition, any material such as cloth or a resin may be used as a material of the inner 710 as long as the auscultatory sound identification training device 100 and the auscultatory sound generation/management device 200 can be provided.

The outer 720 is configured to cover the auscultatory sound identification training device 100 and the auscultatory sound generation/management device 200 installed on the inner 710 from above the inner 710 and to be attachable and detachable to and from the inner 710. Any material such as cloth or a resin may be used as a material of the outer 720. However, it is preferable to use a material capable of delivering an auscultatory sound transmitted to the cover member 130 of the auscultatory sound identification training device 100. In particular, a resin, for example, a urethane resin, etc. is preferably used.

Further, when each auscultatory sound identification training device 100 is accommodated in the pocket of the inner 710 such that the cover member 130 is located in, for example, a chest or an abdomen, and the outer 720 covers the device from above, it is applicable to auscultatory training for a simulated patient in clinical education. That is, since the cover member 130 is located around the chest or the abdomen under the outer 720, and the auscultation vest can be worn on a human body or a doll, it is possible to perform auscultatory training for the heart sound or the lung sound significantly easily in exercise form.

According to the embodiment of the present invention, it is possible to provide an auscultatory sound identification training device and an auscultatory sound identification training system which have simple structure/configurations, are excellent in portability, and exhibit a practical effect that training of indirect auscultation easily using a stethoscope anytime and anywhere can be performed.

In addition, the embodiment of the present invention is excellent in handling property and has an excellent effect that economical provision at low cost is allowed.

Further, according to the embodiment of the present invention, it is possible to provide an auscultatory sound identification training device and an auscultatory sound identification training system enabling remote auscultation.

Furthermore, according to the embodiment of the present invention, since it is difficult to transmit noise from the outside, and a sound emitted inside is audibly checked by a hermetically sealed structure, it is possible to perform auscultatory training under an optimal environment.

(1) A configuration is adopted to include a sounding body for converting a sent electric signal related to auscultatory sound information into an acoustic signal and outputting the converted signal as an auscultatory sound, a mounting plate for mounting the sounding body to surround an outer peripheral portion thereof, and a cover member made of a resin provided on a surface portion side of the mounting plate to cover a front portion side of the sounding body, the cover member having a hardness equivalent to a hardness of a human skin and at least a short width of 45 mm.

(2) A configuration is adopted to include a sounding body for converting a sent electric signal related to auscultatory sound information into an acoustic signal and outputting the converted signal as an auscultatory sound, a mounting member for mounting the sounding body so that a front portion side is directed outward, and a cover member made of a resin provided on a surface portion side of the mounting member to cover the front portion side of the sounding body, the cover member having a hardness equivalent to a hardness of a human skin and at least a short width of 45 mm.

(3) An auscultatory sound identification training device including a sounding body for converting a sent electric signal related to auscultatory sound information into an acoustic signal and outputting the converted signal as an auscultatory sound, a vibration member provided in a contact state on a front portion side of the sounding body, the auscultatory sound from the sound body being directly transmitted thereto, and a cover member made of a resin provided to be in contact with the vibration member, the auscultatory sound being transmitted thereto, in which the sounding body, the vibration member, and the cover member are internally arranged so as not to be in contact with a bottom portion, and the cover member functions to send an auscultatory sound to an outside and vibrate by the auscultatory sound.

(4) In the configuration of item (1) or (2), a resin layer is provided in a vibration member forming the sounding body.

(5) In the configuration of item (3), the auscultatory sound identification training device has a hermetically sealed structure, and an elastic member is provided in the bottom portion.

(6) In the configuration of item (1), (2), (3), (4), or (5), a plurality of sounding bodies is provided.

(7) In the configuration of item (1), (2), (3), (4), (5), or (6), an auscultatory sound generation/management device having storage means that stores various types of auscultatory sound information and output means that sends the auscultatory sound information stored in the storage means to the auscultatory sound identification training device as an electric signal disposed therein is included.

According to the above configurations, it is possible to perform training by indirect auscultation easily using a stethoscope anytime and anywhere. Furthermore, the sounding body and accessories thereof have a simple structure and are excellent in portability.

In addition, according to the above configurations, a large-scale training device is not obtained, and the device becomes small, easy to use, and practical. Additionally, the device is economically feasible at low cost and is useful.

Further, according to the above configurations, remote auscultation is feasible, auscultatory training can be performed anytime and anywhere, and the device is practical and useful.

Furthermore, according to the above configurations, the elastic body makes it difficult to transmit noise from the outside, and auscultatory training can be performed under an optimum environment in which sound emitted inside can be directly heard using a stethoscope by a hermetically sealed structure.

The invention is not limited to the above-mentioned embodiments, and various modifications can be made without departing from a subject matter thereof.

The invention claimed is:

1. An auscultatory sound identification training device comprising:
    a sounding body to convert an electric signal related to auscultatory sound information into an auscultatory sound;
    a vibration member provided to contact the sounding body so that the auscultatory sound generated by the sounding body is transmitted to the vibration member;
    a cover member made of a resin provided to contact the vibration member so that the auscultatory sound is transmitted to the cover member to output the auscultatory sound; and
    a case which has a bottom portion and in which the sounding body, the vibration member and the cover member are provided not to contact the bottom portion.

2. The auscultatory sound identification training device according to claim 1, further comprising:
    an elastic member provided in the bottom portion, wherein the auscultatory sound identification training device has a hermetically sealed structure.

3. The auscultatory sound identification training device according to claim 2, wherein a plurality of sounding bodies is provided.

4. An auscultatory sound identification training system comprising:
    the auscultatory sound identification training device according to claim 2; and
    an auscultatory sound generation/management device having a storage configured to store auscultatory sound information to be output to the auscultatory sound identification training device as the electric signal.

5. The auscultatory sound identification training device according to claim 1, wherein a plurality of sounding bodies is provided.

6. An auscultatory sound identification training system comprising:
    the auscultatory sound identification training device according to claim 5; and
    an auscultatory sound generation/management device having a storage configured to store auscultatory sound information to be output to the auscultatory sound identification training device as the electric signal.

7. An auscultatory sound identification training system comprising:
    the auscultatory sound identification training device according to claim 1; and
    an auscultatory sound generation/management device having a storage configured to store auscultatory sound information to be output to the auscultatory sound identification training device as the electric signal.

8. An auscultatory sound identification training system comprising:
    the auscultatory sound identification training device according to claim 7; and
    an auscultatory sound generation/management device having a storage configured to store auscultatory sound information to be output to the auscultatory sound identification training device as the electric signal.

* * * * *